(12) United States Patent
Moore et al.

(10) Patent No.: US 6,288,266 B1
(45) Date of Patent: *Sep. 11, 2001

(54) HALOGENATED ACRYLATES AND POLYMERS DERIVED THEREFROM

(75) Inventors: George G. I. Moore, Afton; Fred B. McCormick, Maplewood; Mita Chattoraj, Woodbury; Elisa M. Cross, Woodbury; Junkang Jacob Liu, Woodbury; Ralph R. Roberts, Cottage Grove; Jay F. Schulz, Eagan, all of MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/382,300

(22) Filed: Aug. 24, 1999

Related U.S. Application Data

(63) Continuation of application No. 08/872,235, filed on Jun. 10, 1997, now Pat. No. 6,005,137.

(51) Int. Cl.$^7$ ................................................. C07C 69/00
(52) U.S. Cl. ........................ 560/139; 560/140; 526/243; 525/326.4
(58) Field of Search ................................. 560/139, 140; 526/243; 525/326.4

(56) References Cited

U.S. PATENT DOCUMENTS

| | | |
|---|---|---|
| 3,321,515 | 5/1967 | Moore et al. . |
| 3,520,863 | 7/1970 | Anello et al. ................ 260/89.5 |
| 3,544,535 | 12/1970 | Gilbert et al. ................ 260/89.5 |
| 3,668,223 | 6/1972 | Jones ................ 260/343.2 |
| 3,683,027 | 8/1972 | Sianesi et al. ................ 260/594 |
| 3,723,507 | 3/1973 | Anello et al. ................ 260/486 |
| 3,845,102 | 10/1974 | Higuchi et al. ................ 268/479 |
| 3,981,928 | 9/1976 | Pavlik ................ 260/615 |
| 4,010,212 | 3/1977 | Pavlik ................ 260/615 |
| 5,045,397 | 9/1991 | Jensen ................ 428/429 |
| 5,093,888 | 3/1992 | Takezawa et al. ................ 385/141 |
| 5,223,593 | 6/1993 | McAllister et al. ................ 526/245 |
| 5,236,919 | 8/1993 | Crawley et al. ................ 514/349 |
| 5,311,604 | 5/1994 | Rogner et al. ................ 385/14 |
| 5,326,919 | 7/1994 | Paisley et al. ................ 585/241 |
| 5,343,544 | 8/1994 | Boyd et al. ................ 385/46 |
| 5,350,497 | 9/1994 | Hung et al. ................ 204/157.92 |
| 5,384,374 | 1/1995 | Guerra et al. ................ 525/326.4 |
| 5,466,877 | 11/1995 | Moore ................ 562/852 |

FOREIGN PATENT DOCUMENTS

| | | |
|---|---|---|
| 0 230 656 A | 8/1987 | (EP) . |
| 0 249 867 A | 12/1987 | (EP) . |
| 282019 | 9/1988 | (EP) ................ C08F/20/18 |
| 1 547 223 A | 11/1968 | (FR) . |
| 2 623 510 A | 5/1989 | (FR) . |
| 955 127 A | 4/1964 | (GB) . |

OTHER PUBLICATIONS

Werner Storzer et al., "Novel routes to fluorinated ethers containing a fluorosulfonyl group", Journal of Fluorine Chemistry., vol. 58, No. 1, Jul. 1992, Lausanne CH, p. 59–69, XP002056729.

Donald J. Burton et al., "Preparation of alpha–halo–F–2–ketones and F–2–ketones via fluorination of alpha, alpha–dihalo–F–2–ketones", Journal of Fluorine Chemistry, vol. 65, No. 1–2, Nov. 1993, Lausanne Ch, p. 153–156, XP002056730.

W. Groh and A. Zimmermann, *Macromolecules*, 24, (Dec., 1991) p. 6660.

S. R. Sandler and W. Karo, Polymer Synthesis, vol. 1 $2^{nd}$ Ed., Ch. 10 (pp 317–376) Academic Press, Inc., NY (1992).

Smith, Fawcett & Coffman, JACS, 84, p. 4285 (1962).

Zeifman et al., *Izv. Akad Nauk, Ser. Khim*, 2, 464–468 (1992).

*Primary Examiner*—David W. Wu
*Assistant Examiner*—Tanya Zalukaeva
(74) *Attorney, Agent, or Firm*—Philip Y. Dahl

(57) ABSTRACT

Acrylates having a high degree of halogenation, as well as polymers that include one or more mer units derived from such acrylates provide materials having tailorable optical and physical properties. The polymers find utility particularly in optical devices including optical waveguides and interconnecting devices.

11 Claims, 1 Drawing Sheet

HALOGENATED ACRYLATES AND POLYMERS DERIVED THEREFROM

This is a continuation of application Ser. No. 08/872,235 filed Jun. 10, 1997, now U.S. Pat. No. 6,005,137.

BACKGROUND INFORMATION

1. Field of the Invention

This invention relates to acrylates in which a large percentage of hydrogen atoms have been replaced by halogens and to polymers that include mer units derived from such halogenated acrylates.

2. Background of the Invention

Optically transparent polymers, especially those used for telecommunication applications, must have low absorptive loss in the infrared wavelengths, typically 1260–1360 nm and 1480–1580 nm. However, because these wavelengths are close to overtones of carbon-hydrogen bond vibration frequencies, minimization of the number of carbon-hydrogen bonds is desirable. While some organic compounds with few C—H bonds are known, additional considerations of optical transparency, ease of polymerization, refractive index, chemical and mechanical stability, and the need to compete on a cost basis with glass prevent many such compounds from widespread use in polymeric optical devices.

U.S. Pat. Nos. 3,668,233, 3,981,928, and 4,010,212 describe acrylic acid esters (i.e., acrylates), prepared from esterification of acrylic acid with perfluoro-tertiary alkyl alcohols such as perfluoro-t-butyl alcohol, that can be used as inert heat exchange fluids and as homopolymeric water- and/or oil-repellent surface coatings.

European Patent Application No. 282,019 describes highly fluorinated, transparent acrylates specifically tailored for optical articles. These materials are prepared from cyclic or bicyclic alcohols containing few or no carbon-hydrogen bonds.

U.S. Pat. No. 3,544,535 describes the preparation and polymerization of 2-(pentafluorophenyl)hexafluoroisopropyl acrylate. Optical properties of the polymer are not described.

U.S. Pat. Nos. 3,520,863 and 3,723,507 describe a number of perfluorocycloalkyl acrylates and polymers thereof. Use of tertiary alcohols is not reported, and optical properties of the polymers are not discussed.

U.S. Pat. No. 5,045,397 describes the preparation and use of certain adhesives to be used in optical systems. A polymeric adhesive of a specified refractive index is prepared by copolymerization of specified monomers of known refractive indices. While some lightly fluorinated monomers are described, highly fluorinated monomers are not disclosed.

U.S. Pat. No. 5,223,593 describes acrylate monomers and their (co)polymers designed to have low C—H bond density relative to poly(methylmethacrylate) so as to reduce vibrational band intensities in plastic optical fiber cores. Absorbance at 600–1200 nm was reduced, but absorbance at higher frequencies is not reported. The described acrylates were prepared from highly fluorinated primary alcohols.

U.S. Pat. No. 5,093,888 describes a polymeric optical device (specifically, an injection-molded Y-shaped splitter waveguide) that uses an amorphous polymeric adhesive that includes 2,2,2-trifluoroethyl methacrylate having a refractive index of 1.418 to hold optical fibers in a polytetrafluoroethylene spacer containing a fluorinated polyetheretherketone core.

U.S. Pat. No. 5,311,604 describes a method of manufacturing a polymeric optical interconnect. Useful polymers are said to be those transparent to the wavelength of light to be utilized. Listed examples include poly(methylmethacrylate) ("PEMA"), polycarbonates, polyurethanes, polystyrenes, and polyolefins. In one example, a "copolymer of deuterated PMMA-d8 (sic) and tetrafluoropropyl methacrylate" is used to adhere optical fibers to a molded PMMA device.

U.S. Pat. No. 5,343,544 describes a polymeric optical interconnect. The device includes polymeric substrate and covering members that can be fabricated from, for example, a combination of fluorinated and non-fluorinated photopolymerizable (meth)acrylate and di(meth)acrylate monomers. The same combination of monomers is said to be useful for sealing optical fibers in the device. Substitution of fluorines for hydrogen atoms in the polymer is said to be capable of reducing the refractive index of the polymer and to reduce losses in near infrared wavelengths, but no example of a haloacrylate-only system and no indication of the degree to which loss or refractive index can be controlled are given. Copolymerization of two or more monomers is said to be able to provide a copolymer having a tailored refractive index.

Devices used in telecommunication applications (such as those described in '604 and '544, above) preferably meet certain standards for performance, durability, and the like. The standards most commonly referred to in discussing such devices are the so-called "Bellcore Specifications". Requirements for fiber optic branching components include parameters for optical loss (i.e., loss that is in excess over that which is inherent in the device), useable wavelength ranges, resistance to performance variability caused by temperature and humidity, optical cross talk, water immersion, flammability, etc. All such parameters can depend, at least in part, on the materials used to make the device. For example, materials must have very low absorptive losses in the wavelength regions of 1260 to 1360 nm (nominally 1310 nm) and from 1480 to 1580 nm (nominally 1550 nm), over which ranges low losses must be maintained under extreme temperature and humidity conditions. For a 1×2 splitter, the inherent loss is calculated to be 3.01 decibels (dB), where a decibel is defined as —10 $\log(I_o/I_i)$ in which $I_o$ is the intensity of the output and $I_i$ is the intensity of the input. Maximum allowable excess loss in a 1×2 splitter is quantified as, e.g., no more than 0.25 dB per fiber plus no more than 0.5 dB per waveguide junction connecting an input fiber to an output fiber.

Presently available materials other than glass have not proven to be able to meet all, or even most, of these rigid requirements.

SUMMARY OF THE INVENTION

Briefly, the present invention provides halogenated acrylates having the general formula

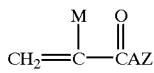

wherein

M is H, $CH_3$, F, Cl, Br, I, or $CF_3$; preferably M is H, F, or Cl; most preferably M is H because of availability, reactivity, and thermal stability;

A is oxygen or sulfur; and

Z can be a group having a maximum of 150 carbon atoms and can be

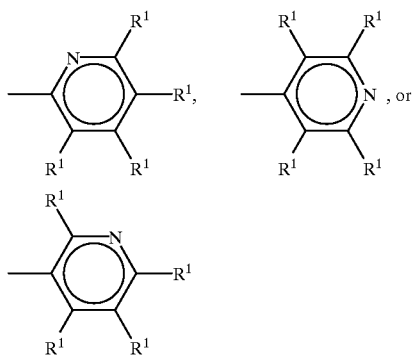

(1)

in which each $R^1$ independently is F, Cl, or Br;

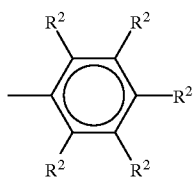

(2)

in which each $R^2$ independently can be
(a) a perfluorinated, perchlorinated, or per(chlorofluoro)
  (i) $C_1$–$C_{20}$ aliphatic group,
  (ii) $C_3$–$C_{20}$ cycloaliphatic group,
  (iii) $C_6$–$C_{20}$ aryl group,
  (iv) $C_7$–$C_{20}$ aralkyl group, and
  (v) $C_7$–$C_{20}$ alkaryl group,
(b) F, Cl, Br, I, Q (defined below), $R^4COO$—, $R^4O$—, —$COOR^4$, —$OSO_2R^4$, or —$SO_2OR^4$, wherein $R^4$ is any group from (a)(i), (a)(ii), (a)(iii), (a)(iv), and (a)(v), or any two adjacent $R^2$ groups together can form a perfluorinated, perchlorinated, or per(chlorofluoro) cycloaliphatic or aromatic ring moiety in which n fluoro or chloro groups optionally can be replaced by $R^2$ groups where n is a whole number in the range of 0 to 25, and $R^2$ is as defined above, wherein Q is

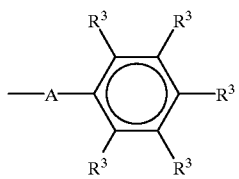

in which A is as defined as above, with the proviso that all $R^2$ groups in the molecule can be the same only when $R^2$ is not Cl, F, Br or I, and each $R^3$ independently can be
(a) a perfluorinated, perchlorinated, or per(chlorofluoro)
  (i) $C_1$–$C_{20}$ aliphatic group,
  (ii) $C_3$–$C_{20}$ cycloaliphatic group,
  (iii) $C_6$–$C_{20}$ aryl group,
  (iv) $C_7$–$C_{20}$ aralkyl group, and
  (v) $C_7$–$C_{20}$ alkaryl group,
(b) F, Cl, Br, I, Q (defined above), $R^4COO$—, $R^4O$—, —$COOR^4$, —$OSO_2R^4$, or —$SO_2OR^4$, wherein $R^4$ is any group from (a)(i), (a)(ii), (a)(iii), (a)(iv), and (a)(v), or any two adjacent $R^3$ groups together can form a perfluorinated, perchlorinated, or per(chlorofluoro) cycloaliphatic or aromatic ring moiety in which n fluoro or chloro groups optionally can be replaced by n $R^3$ groups where n is a whole number in the range of 0 to 25, and $R^3$ is as defined above;

(3)—$C(R_f)_2E$ in which
both $R_f$ groups together can be part of a perfluorinated, perchlorinated, or per(chlorofluoro) cycloaliphatic ring group or each independently can be a perfluorinated, perchlorinated, or per(chlorofluoro)
(a) $C_1$–$C_{20}$ aliphatic groups,
(b) $C_1$–$C_{20}$ cycloaliphatic groups,
(c) $C_6$–$C_{20}$ aryl groups,
(d) $C_7$–$C_{20}$ aralkyl groups, or
(e) $C_7$–$C_{20}$ alkaryl groups,
(f) $C_4$–$C_{20}$ heteroaryl groups,
(g) $C_4$–$C_{20}$ heteroaralkyl groups,
(h) $C_4$–$C_{20}$ heteroalkaryl groups,
wherein the heteroatoms can be one or more of O, N, and S atoms,
with the proviso that at least one $R_f$ group includes one or more of the following:
(1) at least one straight-chain $C_4$–$C_{20}$ aliphatic or $C_4$–$C_{20}$ cycloaliphatic group,
(2) at least one ether oxygen atom, and
(3) at least one branched $C_3$–$C_{20}$ aliphatic group, and E can be $R_f$,

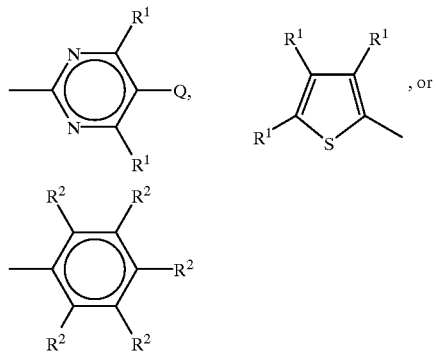

wherein $R^1$, $R^2$, $R_f$, and Q are defined as above; or
(4) —$CR_f(E)_2$,
wherein each E independently is as defined above, and $R_f$ is as defined above.

In another aspect, the present invention provides a polymer that includes at least one mer unit derived from the above-described haloacrylates as well as optical devices and optical materials made from such a polymer.

In yet another aspect, this invention provides di- and tri-functional acrylates as crosslinking agents with low hydrogen content, usually no more than the required three H atoms around each acrylate group.

In yet another aspect, this invention provides ether-containing perhalo-, preferably perfluoro- and perchlorofluoro ketones as intermediates to low H-content acrylates. Preferred compounds include 1,2-dichloroperfluoroethyl ether and 1,1,2-trichloroperfluoroethyl ether derivatives which can be prepared by the direct fluorination of a 1,1-dichloroethyl ether and 1,1,1-trichloroethyl ether, respectively.

In yet a further aspect, this invention provides 1,2-dichloroperfluoro/per(chlorofluoro) ethers useful in the synthesis of the above acrylates and also useful as precursors to perfluorovinyl ether monomers optionally substituted by functional groups. Preferred perfluorinated ketones have the structure $R^5_fOCF_2COCF_3$, $R^5_fOCF_2COCF_2Cl$, and $R^5_fOCF_2COCF_2OR^5_f$, wherein $R^5_f$ is perfluoroalkyl or perfluorooxyalkyl group having from two to twenty carbon atoms.

In this application, the following definitions apply unless a contrary intention is explicitly indicated:

(a) "group" or "compound" or "monomer" or "polymer" or "mer unit" means a chemical species that allows for substitution by conventional substituents that do not interfere with the desired product such as, for example, linear or branched alkyl or haloalkyl groups;

(b) "optical coupler" or "interconnect" means a device that joins one or more input optical fibers to one or more output optical fibers and includes devices such as splitters and combiners;

(c) "acrylate" includes corresponding "methacrylate" and other 2-substituted acrylates throughout this application; and (d) subscript "$f$" refers to a perhalogenated group.

The halogenated acrylates of the present invention have relatively few C—H bonds, usually no more than three (i.e., those around the acrylate unsaturation) or no more than five (around methacrylate unsaturation). This dearth of hydrogens means that these compounds have very little absorption in the infrared wavelengths of interest, i.e., 1260–1360 nm and 1480–1580 nm. Because these materials can be used in optical applications, particularly devices that guide light such as waveguides and optical interconnects, minimizing loss of signal due to absorption by the material of which the device is made is very important and desirable.

Despite the fact that the acrylates of the present invention are highly halogenated, they are relatively easy to polymerize, are optically clear, have low optical loss, are liquids or solids with relatively low melting points or dissolve sufficiently in lower-melting comonomers, provide amorphous polymers with good thermal stability and high molecular weights, and provide polymers (typically copolymers) having indices of refraction that effectively match those of glass optical fibers. These characteristics make them excellent candidates for use as materials in polymeric optical devices, especially waveguides and optical couplers.

Presently available optical devices made from glass are manufactured in one-at-a-time, handwork operations that are very labor intensive and prone to low productivity. Polymers of the invention can be processed automatically by known polymer processing methods into optical devices that are physically robust and are substantially identical, leading to significant improvements in product reliability and economics. Polymeric optical devices of the present invention can be mass produced and can be handled under severe field conditions without undue damage and/or loss of properties.

DETAILED DESCRIPTION OF PREFERRED EMBODIMENTS

Figure 1:
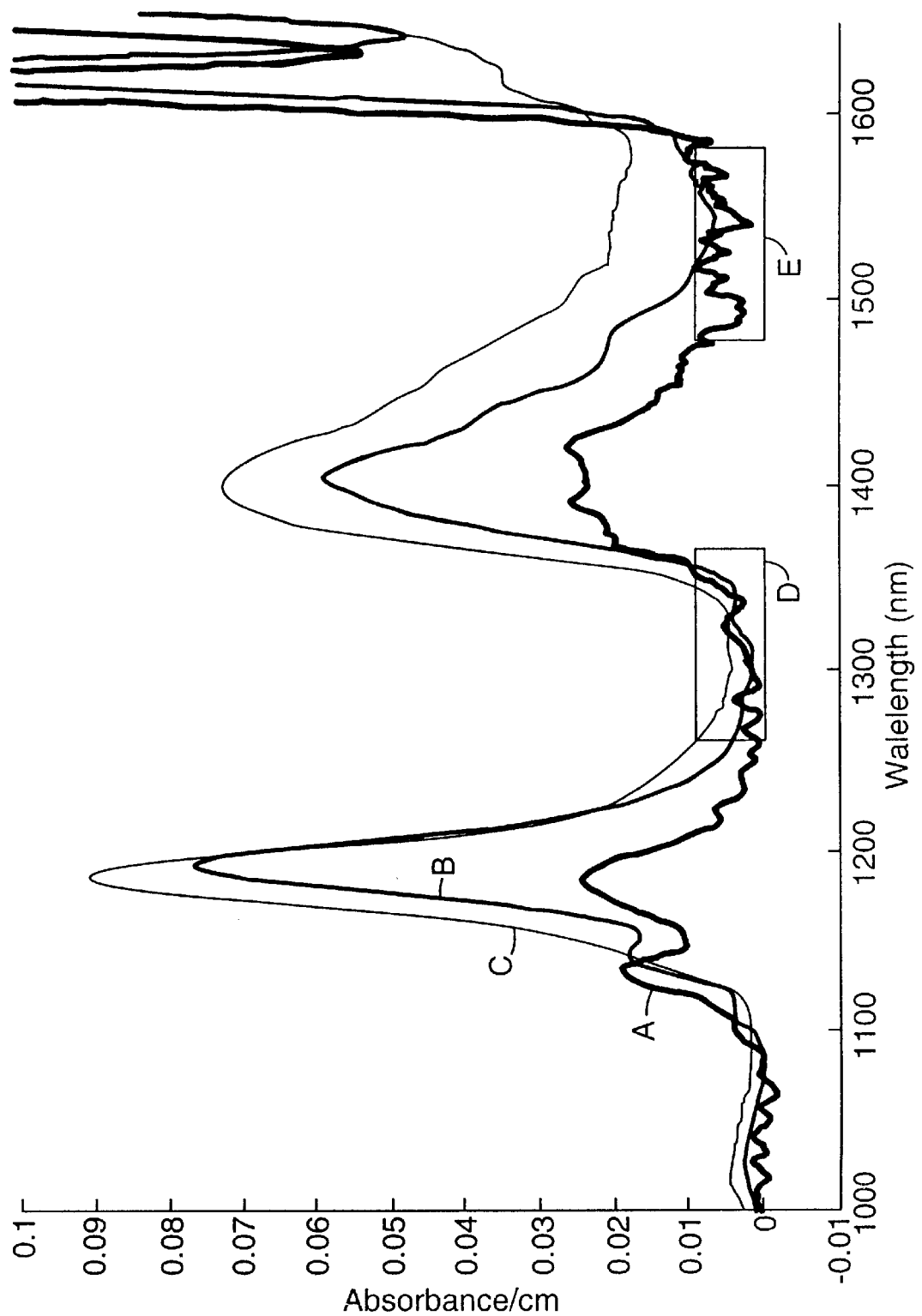
FIG. 1 is a comparison of absorption vs. wavelength plots of a polymer derived from one embodiment of the halogenated acrylates of the present invention with two comparative halogenated polyacrylates.

Halogenated acrylates of the present invention are useful for various optical applications. They display several highly desirable characteristics including ease of polymerization, optical clarity, favorable melting points, and polymers therefrom exhibit very little absorption in critical infrared regions (i.e., 1260–1360 nm and 1480–1580 nm), thus minimizing optical loss due to absorption. When halogenated acrylates of the present invention are polymerized, or when two or more are copolymerized, the resulting polyacrylate is amorphous, has good thermal stability, has relatively high molecular weight, and can have an index of refraction that effectively matches that of a glass optical fiber. Further, halogenated acrylates of the invention can be copolymerized to prepare copolymers having specifically desired physical properties, such as refractive index ($n_\lambda$), glass transition temperature (Tg), optical absorption, etc. In spite of published theories of predicting such properties based on additivity considerations (e.g., the Fox equation for Tg), we have found that certain combinations of monomers, particularly those having high molecular bulk, give copolymers having unpredicted refractive indices, and that physical properties and chemical reactivities of these highly halogenated monomers cannot be predicted a priori. Further, we have found that synthesis and measurement are required to determine the exact refractive index and reactivity of these highly halogenated monomers, and that copolymers must be prepared in order to determine their precise refractive index and melting point; calculations and predictions are insufficient. Table 1, below, shows the disparity between calculated and observed refractive indices for a number of homopolymers of the invention.

Halogenated acrylates of the present invention have the general formula

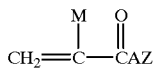

wherein M, A and Z are as defined above.

The portion of the molecule other than the Z moiety defines a typical acrylate when A is oxygen and a thioacrylate when A is sulfur. As those skilled in the art of polymer science are well aware, acrylates are a broad class of polymerizable materials, the chemistry of which is well defined.

Although M typically is H, other substituents such as $CH_3$, F, Cl, Br, I, or $CF_3$ can be used in place of hydrogen. However, any such substitution should be done while keeping in mind the desired performance characteristic(s) of the material (e.g., polymer index of refraction, ease of polymerization, liquidity at the temperature(s) of use, very little absorption in the critical infrared regions, monomer availability, and cost, etc.).

Many acrylates meet several of the aforementioned criteria regarding acceptable materials. For example, acrylates have relatively low melting points and can be polymerized to amorphous polymers with high molecular weights. However, heretofore available acrylates have not been able to meet those criteria relating to optical performance. Specifically, such acrylates have had unacceptably high absorption in the aforementioned infrared wavelength regions. In contrast, halogenated acrylates of the present invention have acceptably low absorption in these wavelength regions.

In the general formula set forth above, A can be either oxygen or sulfur. (Although the term "acrylate" normally would include only those compounds where A is oxygen, for present purposes, the term includes those compounds where A is sulfur.) For reasons of availability of starting materials, hydrolytic stability, and potential odors, those compounds where A is sulfur are not as preferred as those where A is oxygen.

The Z moiety in the above formula serves at least two important functions. First, it assists in tailoring the index of refraction of the polymerized halogenated acrylate. Because the index of refraction of optical fiber cores and cladding layers generally fall in the range of 1.44 to 1.46, this is a desirable index of refraction range for optical materials of the invention. Preferably, homopolymers prepared from the halogenated acrylates of the present invention have an index of refraction of between about 1.36 and about 1.56. Further, acrylate monomers can be mixed to provide copolymers having an index of refraction in the desired range. Since the index of refraction of most glass used in optical fiber cores is approximately 1.457, a preferred index of refraction of a copolymer of the invention can be approximately 1.450. It is to be appreciated that in an optical device the index of refraction of a core desirably is slightly higher than the clad, and the core index of refraction desirably matches the index of refraction of an optical fiber core, which fiber is connected to the device. Typically, the index of refraction of the clad in a device can be slightly less than that of the core (the difference preferably is about 0.007).

Second, the bulk of the Z moiety assists in keeping low the weight percentage of hydrogen in the halogenated acrylates of the present invention. To reach acceptably low absorption in the infrared wavelength regions of interest (i.e., those wavelengths where overtones of C—H bond vibration frequencies absorb), keeping the weight percentage of hydrogen in the compound as low as possible is desirable. An empirical rule regarding the relationship between molar volume and absorption loss at 1480 nm has been developed through experience: to keep absorption loss less than 0.1 dB/cm (at 1480 nm), a haloacrylate of the invention wherein A is O and M is H desirably has a molar volume of at least 150 mL/mole, more preferably at least 200 mL/mole, and even more preferably at least 250 mL/mole. The corresponding halomethacrylates wherein A is O and M is $CH_3$ require higher molar volumes to meet the 0.1 dB/cm (at 1480 nm) absorption loss criterion. To assist in meeting this target molar volume, Z serves the important function of increasing the molecular volume without adding hydrogen atoms to the halogenated acrylate of the present invention so that the effect of the hydrogen atoms surrounding the double bond is minimized. Copolymers of halogenated acrylates where one or more of the monomers includes a relatively small Z group and one or more monomers includes a relatively large Z group, such that the overall molar volume of the copolymer is at least 150 mL/mole, also are within the scope of the present invention.

Finally, the Z group influences the chemical stability and melting point of the monomer and resulting (co)polymer(s). In particular, we have found that any one of three types of substituents on the ester portion of the acrylate are preferred: inclusion of an ether oxygen in an aliphatic or aromatic group; mixtures of positional isomers of aromatic substituents; and branched aliphatic moieties; as well as combinations thereof As mentioned previously, Z can be one of four types of groups. First, Z can have the general formula —$C(R_f)_2E$, wherein each $R_f$ group and E are as defined above.

As to each $R_f$, examples of potentially useful $C_1$–$C_{20}$ acyclic aliphatic groups include methyl, methoxymethyl, ethoxymethyl, propoxymethyl, butoxymethyl, ethyl, propyl, butyl, pentyl, hexyl, heptyl, octyl, nonyl, decyl, undecyl, dodecyl, methoxyethoxymethyl (i.e., $CF_3OCF_2CF_2OCF_2$), methoxypropoxymethyl, methoxyethoxyethoxymethyl, ethoxyethoxymethyl, ethoxyethyl, and methoxyethyl groups. For each alkyl group named having more than two carbon atoms, isomers thereof, particularly branched isomers, are included in this definition. Further, all alkyl groups are fluoroalkyl, chloroalkyl, or fluorochloroalkyl groups; that is, all hydrogen atoms have been replaced by fluorine atoms, chlorine atoms, or combinations thereof Examples of potentially useful $R_f$ groups comprising $C_3$–$C_{20}$ cycloaliphatic groups include cyclopropyl, cyclobutyl, cyclopentyl, cyclohexyl, cycloheptyl, cyclooctyl, bicyclo{2.2.1}hexyl, bicyclo{2.2.2}octyl, bicyclo{3.2.2}nonyl, and bicyclo{4.4.0}decyl. Any of the cycloaliphatic groups can include $C_1$–$C_{10}$ straight-chain or branched aliphatic carbon substituents, as well as above-named acylic aliphatic groups, at any position thereof, consistent with steric bulk considerations. As noted, all hydrogen atoms of the cycloaliphatic groups are to be replaced by fluorine atoms, chlorine atoms, or combinations thereof.

Examples of $R_f$ groups as potentially useful $C_6$–$C_{20}$ aryl groups include phenyl, naphthyl, indenyl, biphenyl, anthracyl, phenanthryl, and fluorenyl groups, wherein all hydrogen atoms have been replaced by fluorine atoms, chlorine atoms, bromine atoms, or combinations thereof.

Examples of $R_f$ groups as potentially useful $C_7$–$C_{20}$ alkaryl groups include methylphenyl, ethylphenyl, methylnaphthyl, dimethylphenyl, indanyl, and butylphenyl groups, wherein all hydrogen atoms have been replaced by fluorine atoms, chlorine atoms, bromine atoms, or combinations thereof.

Examples of $R_f$ groups as potentially useful $C_7$–$C_{20}$ aralkyl groups include phenethyl and benzyl groups, wherein all hydrogen atoms have been replaced by fluorine atoms, chlorine atoms, bromine atoms, or combinations thereof Examples of potentially useful $R_f$ groups comprising $C_4$–$C_{20}$ heteroaryl, heteroaralkyl and heteroalkaryl groups include any cyclic aromatics comprising at least one oxygen, nitrogen or sulfur atom in the ring, including those having $C_1$–$C_{10}$ straight-chain or branched aliphatic carbon substituents, as well as above-named acylic aliphatic groups, at any position thereof, consistent with steric bulk considerations. Useful heteroaromatics include furan, thiophene, pyrrole, 1,2- and 1,4-pyran, 1,2- and 1,4-thiopyran, pyridine, oxazole, isoxazole, thiazole, isothiazole, imidazole, pyrazole, 1,2,3- and 1,2,4-triazole, tetrazole, pyridazine, pyrimidine, pyrazine, 1,4-dioxin, 1,4-dithiin, 1,2-, 1,3-, and 1, 4-oxathiin, 1,2-, 1,3-, and 1,4-oxazine, and 1,2-, 1,3-, and 1,4-thiazine. It is to be appreciated that all hydrogen atoms of each of the above-named heteroaryl ring systems and their alkyl-substituted analogs are to replaced by fluorine atoms, chlorine atoms, bromine atoms, or combinations thereof In addition to the single-ring heteroaryl, heteroaralkyl and heteroalkaryl groups, $R_f$ groups can comprise analogous fused-ring heteroaromatic compounds including benzofuran, thionaphthene, indole, isothionaphthene, isobenzofuran, isoindole, 1,2- and 1,4-benzopyran, 1,2- and 1,4-benzothiopyran, quinoline, isoquinoline, cinnoline, quinazoline, quinoxaline, phthalazine, benzoxazole, benzothiazole, benzimidazole, benzpyrazole, benzotriazole, and numerous fused ring groups comprising three or more rings comprising at least one N-, O-, or S-atom, including any of these having $C_1$–$C_{10}$ straight-chain or branched aliphatic carbon substituents, as well as above-named acylic aliphatic groups, at any position thereof, consistent with steric bulk considerations. It is to be appreciated that all hydrogen atoms of each of the above-named heteroaryl ring systems and their alkyl-substituted analogs are to replaced by fluorine atoms, chlorine atoms, bromine atoms, or combinations thereof.

Some $R_f$ groups that can be particularly useful for certain applications include methyl, chloromethyl, ethoxymethyl, (2-chloroethoxy)methyl, trichloroethoxymethyl, hexyl, cyclohexyl, and butoxymethyl.

$R_f$ groups including branched aliphatic or alkyl groups may be preferred when mixtures of branched isomers or stereoisomers can be obtained that result in lowering of the haloacrylate melting point to provide ease of handling of the monomers.

E represents one of four substituents. Specifically, E can be $R_f$,

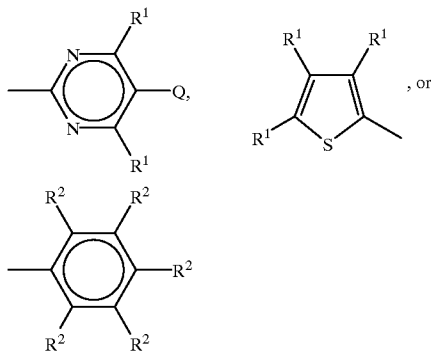

wherein $R^1$, $R^2$, $R_f$, and Q are defined as above. In a preferred embodiment, each $R^1$ or $R^2$ is F.

Z also can have any of the formulae

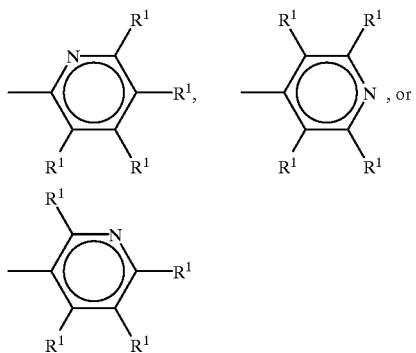

in which each $R^1$ is defined as above. Where Z has this formula, preferred compounds include those where each $R^1$ is either F or Cl.

Third, Z also can have the formula

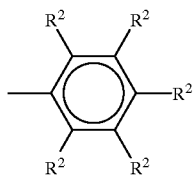

wherein each $R^2$ is as previously defined.

In a preferred embodiment, at least one $R^2$ is F, $OC_6F_5$, $SC_6F_4CF_3$, $OC(O)C_6F_5$, or $OSO_2C_4F_9$.

Fourth, Z can have the formula $CR_f(E)_2$ wherein each E and $R_f$ are as previously defined.

Some preferred halogenated acrylates of the present invention having homopolymers with refractive indices greater than or equal to 1.457 (i.e., "high index materials") are represented by the following formulae:

I

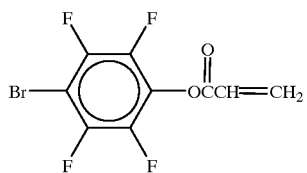

II

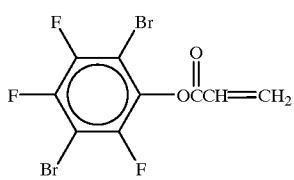

III

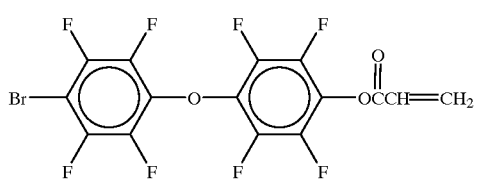

IV

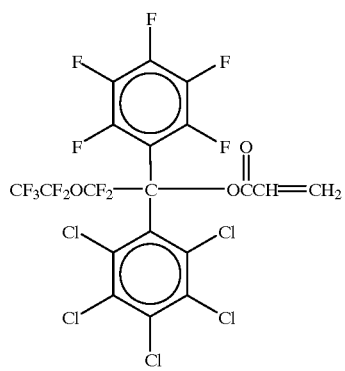

V

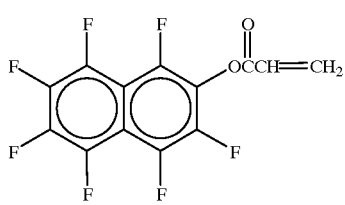

VI

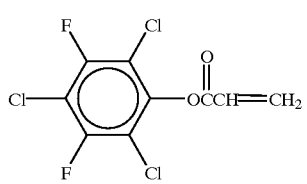

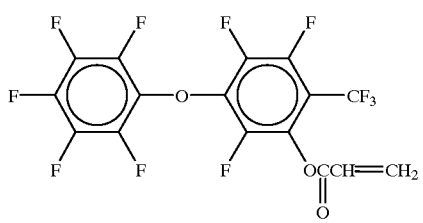
VII

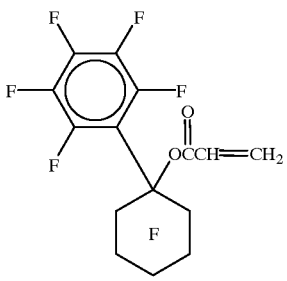
XI

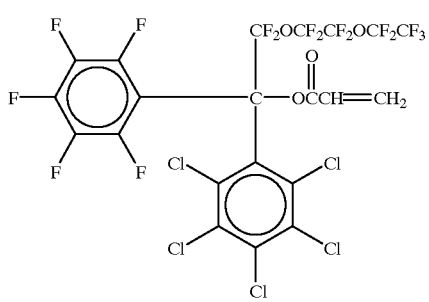
XVI

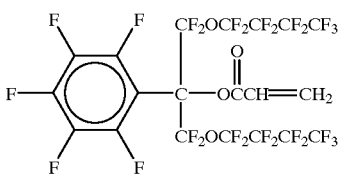
XII

Some preferred halogenated acrylates of the present invention having homopolymers with refractive indices less than 1.457 (i.e., "low index materials") are represented by the following formulae:

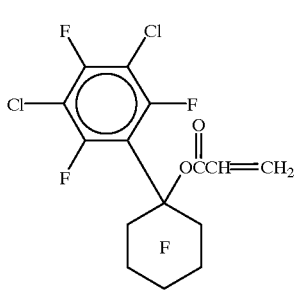
XIII

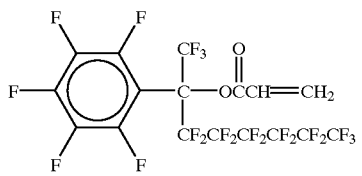
VIII

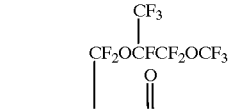
XIV

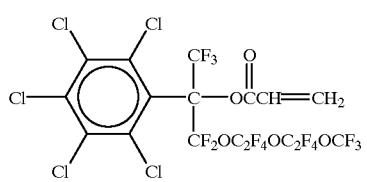
IX

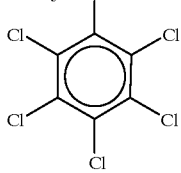

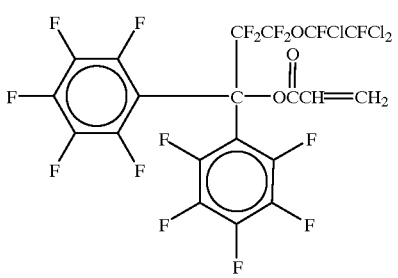
XV

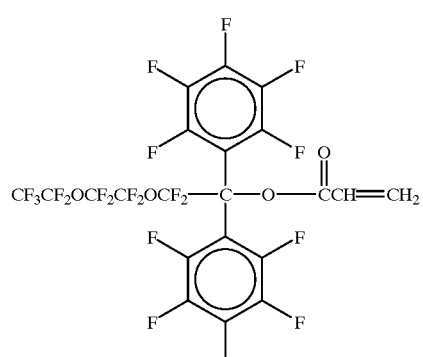
X

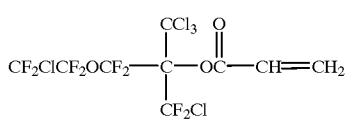
XVII

In addition to the acrylate monomers shown above, the following tertiary carbinols can easily be converted into the corresponding acrylates, the homopolymers of which are predicted to be low index materials:

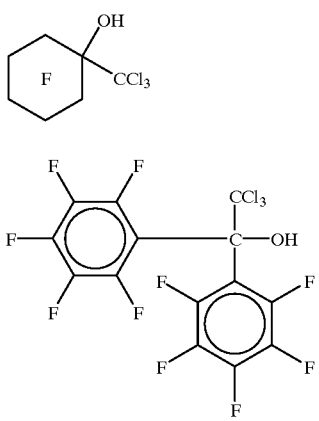

XVIII

XIX

In the above formulae,

represents a cyclohexyl ring in which all hydrogen atoms are replaced by fluorine atoms (i.e., a perfluorocyclohexyl group).

Many preferred halogenated acrylate monomers of the invention include at least one perfluoroether moiety. An ether linkage allows ready variation of the structure of a starting material to be fluorinated and of the fluorinated product. It has been found that the perfluoroether group provides favorable physical properties, such as low melting point or liquidity at 23° C., while allowing control of the refractive index of the corresponding homopolymer and related copolymers by control of structure and substituents.

Homopolymers prepared from these acrylates have characteristic indices of refraction. Accordingly, one wishing to use one or more of these compounds (or any of the halogenated acrylates of the present invention) can choose as halogenated acrylate the homopolymer of which has an index of refraction that matches that which is desired or can choose two or more of these acrylate monomers and copolymerize them so as to provide a polymer that has the desired index of refraction.

FIG. 1 shows absorption versus wavelength plots for three halogenated polyacrylates: poly(perfluorophenylacrylate) (PFPA) (comparative tracing C), poly (perfluorophenylthioacrylate) (PFPTA)(comparative tracing B), and compound VIII of the present invention (tracing A), above. PFPA is commercially available from Polysciences, Inc. (Warrington, Pa.) whereas PFPTA and compound VIII can be prepared by, for example, reaction of acryloyl chloride with pentafluorothiophenol or 2-(pentafluorophenyl)-2-perfluorooctanol, respectively. The aforementioned wavelength regions of interest as well as the acceptable absorption limits in those wavelength regions (imposed by the aforementioned Bellcore specifications) are represented by boxes D and E. As is apparent, all three of the polyacrylates have acceptable (i.e., very low) absorption in the 1310 nm region, but only compound VIII has a completely acceptable absorption profile in the 1550 nm region.

Halogenated acrylates of the present invention can be prepared by reacting an acrylic acid derivative such as acryloyl chloride or acrylic anhydride with a perhalogenated alcohol, alkoxide, or alkoxy-substituted alcohol in the presence of an organic base (e.g., a tertiary amine). Using 2-acryloyloxyheptafluoronaphthalene (compound V) as an example, one can react heptafluoro-2-naphthol with acryloyl chloride and triethylamine in an appropriate solvent such as acetonitrile. (See Example 1, below, for more details.) Choice of solvent(s), temperature, pressure, and other reaction variables are within the level of skill possessed by the ordinarily skilled artisan discussed below.

Perhalogenated alkoxides may be prepared from the corresponding perhalogenated alcohols by treatment with base, or by treatment of a perhalogenated carbonyl compound with an alkali metal fluoride (e.g. KF) or perhalogenated carbanion sources such as organometallic reagents (e.g., organo lithiums or Grignard reagents). Perhalogenated alcohols or carbonyl compounds may be prepared by the following methods:

1) Addition of a perhalogenated organometallic compound to a perhalogenated ketone (e.g. $C_6F_5MgCl + R^6_fCOR^6_f \rightarrow \rightarrow R^6_6R^6_fC_6F_5COH$, where each $R^6_f$ group independently can be a perhalogenated straight-chain, branched, or cyclic aliphatic group containing from 1 to 20 carbon atoms and may contain up to 5 ether oxygen atoms). The perhalogenated ketone may be prepared by similar addition of a perhalogenated organometallic compound to a perhalogenated acid fluoride, or may be prepared by direct fluorination of an ester of a secondary alcohol followed by cleavage of the resulting perhalogenated secondary ester.

2) Displacement of a fluorine atom by a hydroxy (or latent hydroxy) on a perhalogenated arene compound.

A preferred class of perhalogenated alcohols or ketones is ether-containing perhalogenated alcohols or ketones. These may be prepared by direct fluorination of an ether-containing precursor ester of a primary or secondary alcohol. For example, they may be prepared by reaction of an alcohol and either propylene glycol (Scheme 1) or epichlorohydrin (Scheme 2) to produce a secondary alcohol, which may then be acylated, fluorinated by direct fluorination, and the resulting perhalogenated ester cleaved by any of the methods described in U.S. Pat. No. 5,466,877, incorporated herein by reference. Perfluorinated ketones of the structure $R^7_fOCF_2COCF_3$, $R^7_fOCFCOCF_2Cl$, and $R^7_fOCF_2COCF_2OR^7_f$ are novel where $R^7_f$ is a linear perfluoroalkyl or perfluorooxyalkyl group having from two to twenty carbon atoms. These compounds are especially useful in preparing the acrylates of this invention to impart a low Tg and high molar volumes.

Reaction Scheme 1

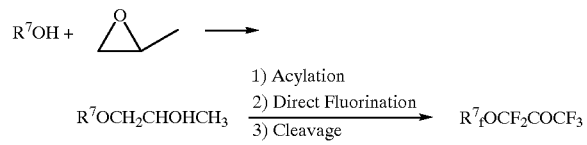

or

Reaction Scheme 2

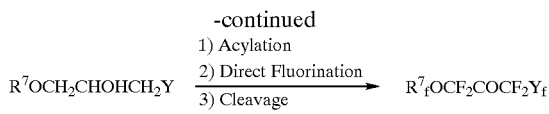

wherein $R^7$ is a linear alkyl or oxyalkyl group which can be terminated by any of —$CH_3$, —$CH(CH_3)_2$, —$C(CH_3)_3$, —$OCH_3$, —$OCH(CH_3)_2$, or —$OC(CH_3)_3$, wherein each $R^7_f$ is the perhalogenated analog of $R^7$, $R^7$ and $R^7_f$ groups having from 1 to 20 carbon atoms, and Y can be Cl, $OR^7$ and $Y_f$ can be Cl or $OR^7_f$. Preferred classes of the perfluorinated ether ketone intermediates are those mono- and diethers in which $R^7_f$ is a perfluoro or per(chlorofluoro)alkyl group of 2–12 carbons and containing up to 5 ether oxygens. Similarly, direct fluorination of the di- or trimesters can lead to di- or tri-ketones.

Halogenated acrylates containing bromine or chlorine in addition to fluorine are useful in increasing the refractive index of the corresponding homo- and copolymers. Chlorofluoroalkyl acrylates may be prepared by the previously described methods from either chlorofluoroketones or chlorofluoroacyl halides. See Example 24. Higher amounts of chlorine in the acrylate are especially useful in raising the refractive index. Surprisingly, it has been found that 1,1-dichloroethoxy ethers and 1,1,1-trichloroethoxy ethers, when subjected to direct fluorination, undergo a rearrangement to produce 1,2-dichloro-perfluoroethoxy ethers and 1,1,2-trichloroperfluoroethoxy ethers respectively. See Examples 11 and 21, and Table 4, compounds 4-2, 4-3, and 4-22. This rearrangement is illustrated in one embodiment, as follows:

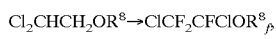

and

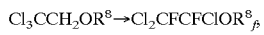

wherein $R^8$ is a $C_1$–$C_{20}$ alkyl- or acyl-containing group optionally containing up to 5 ether oxygen atoms and $P^8_f$ is the corresponding perhaloalkyl or perhaloacyl-containing group, optionally containing up to 5 ether oxygen atoms. Perhaloalkyl or perhaloacyl-containing esters can be cleaved to produce perhaloketones and perhaloacid fluorides as previously described.

Preferred compounds have the formulae $ClCF_2CFClOR^8_f$ and $Cl_2CFCFClOR^8_f$ and are made by direct fluorination of compounds of the formulae $Cl_2CHCH_2OR^8$ and $Cl_3CCH_2OR^8$, respectively, wherein $R^8$ can be a $C_1$–$C_{20}$ alkyl- or acyl-group optionally containing up to 5 ether oxygen atoms and $R^8_f$ can be the corresponding perfluoroalkyl or perfluoroacyl-containing group, optionally containing up to 5 ether oxygen atoms.

The rearrangement is surprising in view of the known instability of α-chloro ethers (see Adcock, et al., U.S. Govt. Report #AD139958 (1984)). These 1,2-dichloroperfluoroethyl ethers and 1,1,2-trichloroperfluoroethyl ethers are useful as solvents and in the preparation of perfluoro- and chloroperfluorovinyl ethers (see U.S. Pat. No. 5,350,497). A preferred subset of these 1,2-dichloro perflouro/per(chlorofluoro) ethers is that in which the $R^8_f$ group contains 1 to 12 carbon atoms and up to 5 ether oxygen atoms. Another preferred subset is that in which the preferred $R^8_f$ group also contains a COF or $SO_2F$ group.

Refractive index and optical absorbance data for several of the compounds whose structures are shown above are given in Table 1, below.

TABLE 1

| Cpd | Example | Homo-polymer $n_{1.31}$ | Homo-polymer $n_{1.31}$ calc | Homopolymer average abs/cm[1] | | Homopolymer abs/cm >0.01[2] | |
|---|---|---|---|---|---|---|---|
| | | | | 1260–1360 nm | 1480–1580 nm | 1260–1360 nm | 1480–1580 nm |
| I | 6 | 1.515 | 1.523 | .004 | .012 | 1350–1360 | 1480–1580 |
| IV | 2 | 1.488 | 1.465 | — | — | — | — |
| V | 1 | 1.523 | 1.487 | .006 | .012 | 1343–1360 | 1480–1580 |
| VI | 5 | 1.547 | 1.550 | .003 | .005 | 1350–1360 | 1480–1485 |
| VII | 4 | 1.465 | 1.452 | .002 | .008 | 1352–1360 | 1480–1500 |
| VIII | 22 | 1.380 | 1.348 | .003 | .006 | 1357–1360 | none |
| IX | 9 | 1.444 | 1.405 | — | — | — | — |
| X | 3 | 1.424 | 1.386 | .006 | .06 | 1350–1360 | 1480–1580 |
| XI | 7 | 1.418 | 1.386 | .004 | .002 | 1340–1360 | none |
| XIII | 15 | 1.368 | 1.331 | — | — | 1345–1360 | - |
| | 8 | 1.446 | 1.421 | .003 | .003 | 1345–1360 | none |
| | 10 | 1.503 | 1.492 | .006 | .007 | 1348–1360 | 1480–1500 |
| | 11 | 1.441 | 1.425 | .003 | .003 | 1355–1360 | none |

[1]Average Abs/cm is the average light absorption per centimeter over the wavelength region noted. The target value is <0.01.
[2]Abs/cm >0.01 indicates those parts of the wavelength region where absorption/cm exceeds 0.01.
(—) in Table 1 and succeeding Tables means no measurement taken.

The data of Table 1 show that a number of candidate haloacrylates have acceptably low absorbances in the target wavelength regions. In addition, these data show that homopolymer refractive index calculations (W. Groh and A. Zimmermann, *Macromolecules,* 24, (December, 1991), p. 6660) cannot predict the observed refractive index, particularly in light of a need to predict refractive index with accuracy in the third decimal point.

As mentioned previously, the halogenated acrylates of the present invention are relatively easy to polymerize. Like most acrylates, they are free radically polymerizable, often in less-than-rigorous conditions. In other words, although oxygen normally must be excluded from the area where an acrylate polymerization is performed, other materials (e.g., water) need not be so excluded.

As with most acrylates, the free radical polymerization of the halogenated acrylates of the present invention can be initiated by heat or by light, optionally but preferably in the presence of a thermal or photo initiator, respectively. Of these two types of initiation, photoinitiation, particularly UV-type photoinitiation, is preferred. In choosing an initiator, consideration of the aforementioned optical loss goals should be considered. For instance, certain UV initiators are highly absorptive in near infrared wavelengths. One UV initiator that has not proven to be especially absorptive in the wavelengths of interest is 2,2-diethoxyacetophene, Ph-C(O)CH(OCH$_2$CH$_3$)$_2$, wherein Ph is phenyl, hereinafter referred to as DEAP.

As with synthesis details discussed previously, choice of solvent(s), temperature, pressure, and other polymerization conditions are within the level of skill possessed by the ordinarily skilled artisan. Nevertheless, further details on similar polymerizations can be found at, for example, S. R. Sandler and W. Karo in *Polymer Syntheses, Vol 1*, 2nd Ed., Ch. 10 (pp 317–376) Academic Press, Inc., New York (1992).

Optionally, halogenated acrylate polymers of the invention may be crosslinked. Physical property changes achieved by crosslinking acrylate polymers include elevated Tg, increased strength, reduced swelling when exposed to solvent or other small molecules, and reduced flexibility. All of these may be highly desirable in achieving the "Bellcore Specifications" requirements for optical branching components prepared from acrylates of this invention. Typical acrylate crosslinkers have C—H bonds in addition to those in the acrylate functionality and may detrimentally affect optical absorbances in the important 1260 to 1360 nm and 1480 to 1580 nm wavelength regions (supra). Thus, there is a need for polyfunctional acrylate crosslinkers with fewer C—H bonds in the molecule, preferably with CH only in the acryloyl group and on the α-carbon atoms of the polyol moiety, more preferably limiting the C—H bonds to only those of the acrylate groups (i.e., no other C—H bonds in the molecule). In an optical device, the crosslinker may be present at a relatively minor component and, as such, a higher hydrogen content can be tolerated. Acrylates prepared from perhalogenated aromatic polyols fit this criterion. Illustrative examples of these polyfuinctional acrylates include tetrafluorohydroquinone diacrylate (XX), tetrafluororesorcinol diacrylate (XXI), and octafluoro-4,4'-biphenol diacrylate (XXII). Acrylates of other halogenated (chlorinated or brominated) aromatic polyols may also be useful as crosslinkers of this invention. The corresponding polyfunctional homologous methacrylate crosslinkers may be substituted for any of the acrylate crosslinkers noted herein.

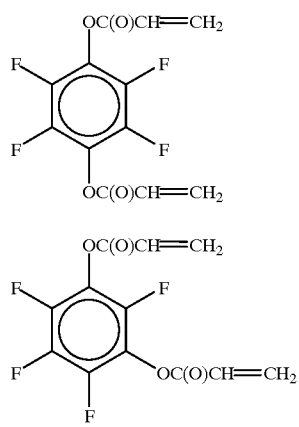

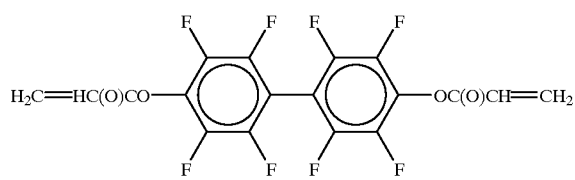

A number of brominated aromatic polyols may be readily purchased or can be synthesized, e.g., by the reaction of bromine with an arornatic polyol as is known in the art. Reaction of the brominated aromatic polyol with, for example, acryloyl chloride in the presence of a base such as triethylamine provides the desired acrylates of the brominated aromatic polyols. Illustrative examples of acrylated perhalogenated aromatic polyols include tetrachlorohydroquinone diacrylate, tetrabromocatechol diacrylate (XXIII), tetrachlorocatechol diacrylate, tetrabromoresorcinol diacrylate, tetrachlororesorcinol diacrylate, tribromophloroglucinol triacrylate (XXIV), tribromopyrrogallol triacrylate (XXV), and tribromo-1,2,4-benzenetriol triacrylate (XXVI).

Tribromoresorcinol diacrylate and trichlororesorcinol diacrylate can also be useful as crosslinkers. They may be useful in optical devices where the number of hydrogen atoms is less important.

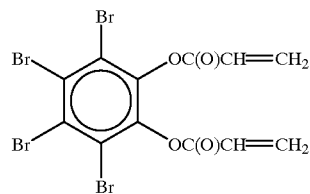

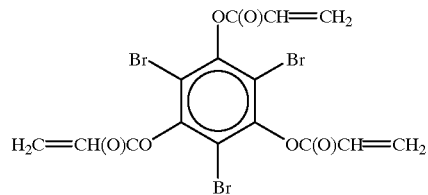

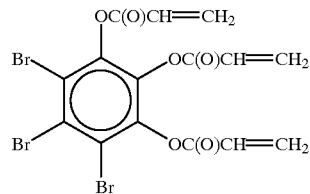

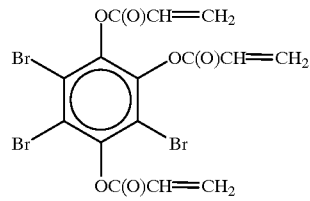

Non-aromatic acyclic aliphatic halogenated polyol polyacrylates may also be useful as crosslinking agents in the invention. Polyacrylates can be prepared by, e.g., the reaction of a perhalogenated polyol with an acryloyl halide, preferably acryloyl chloride. Perhalogenated polyols can be prepared by the perfluorination of an aliphatic hydrocarbon-polyols or a halogenated, preferably chlorinated, aliphatic polyol by known fluorination methods, such as direct fluorination.

Acyclic aliphatic halogenated polyol polyacrylates can have the general formula $R^9_f(CR^{18}R_fOC(O)CH=CH_2)_q$, wherein $R^{18}$ can be H or F, $R_f$ is as previously defined, q can be a whole number of 2 or greater, preferably from 2 to 6, more preferably from 2 to 4, and $R^9_f$ preferably is an acyclic aliphatic halogenated group, free of ethylenic or other carbon-carbon unsaturation, having at least 1 carbon atom and optionally can comprise up to 50, preferably up to 10, non-carbon atoms such as oxygen, nitrogen, and sulfur in the aliphatic chain. $R^9_f$ can comprise an oligomeric polyether, oligomeric polyamine, oligomeric polythiol or polyetheramine, such that the total number of atoms in the $R^9_f$ chain (i.e., the combination of carbon atoms and linking oxygen, nitrogen or sulfur atoms) can be up to 150, preferably up to 50, more preferably up to 25, and most preferably no more than 20. Halogen atoms comprising the $R^9_f$ group can be fluorine, chlorine or bromine, preferably fluorine or chlorine, more preferably a combination of fluorine and chlorine, and most preferably exclusively fluorine.

Representative acyclic aliphatic halogenated polyol polyacrylates are represented by the following formulae of fluorinated acrylates:

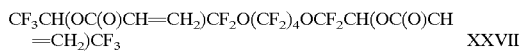

$$CF_3CH(OC(O)CH=CH_2)CF_2O(CF_2)_4OCF_2CH(OC(O)CH=CH_2)CF_3 \quad\quad XXVII$$

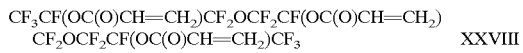

$$CF_3CF(OC(O)CH=CH_2)CF_2OCF_2CF(OC(O)CH=CH_2)CF_2OCF_2CF(OC(O)CH=CH_2)CF_3 \quad\quad XXVIII$$

Halogenated acrylates of the present invention are useful in the preparation of polymers wherein the refractive index and the optical loss of the polymer must be carefully controlled. Polymers and copolymers prepared from the monomers find use in the manufacture of optical devices such as splitters, couplers, light guides, and waveguides. In addition, (co)polymers of the present invention find use as adhesives and index matching compounds for joining optical elements such as lenses, mirrors, optical fibers, light guides, and waveguides. (Co)polymers of the invention find further use as cladding and/or protective materials for optical devices such as those named above as well as optical fibers.

In addition to the aforementioned utilities, the inventive monomers and polymers are useful in a variety of applications such as flame retardants, protective coatings, and adhesives. Acrylates from brominated aromatic polyols can have utility in raising the refractive index of any acrylate system requiring crosslinking and/or flame resistance.

Objects and advantages of this invention are further illustrated by the following examples. The particular materials and amounts thereof, as well as other conditions and details, recited in these examples should not be used to unduly limit this invention.

EXAMPLES

Unless otherwise noted, all materials are commercially available from Aldrich Chemical Co. (Milwaukee, Wis.). "Room temperature" or "ambient temperature" means about 21° C. All chemical structures synthesized were confirmed by spectroscopic analysis.

Test Methods

Glass Transition Temperature (Tg)

Polymer films were prepared from liquified monomers (or monomer mixtures) that were doped with 0.2–0.5% by weight, based upon the total weight of polymerizable monomer(s), of a photoinitiator, preferably PhC(O)CH(OCH$_2$CH$_3$)$_2$ (DEAP), syringe-filtered, deoxygenated, placed between two silicon-treated polyethylene terephthalate (PET) release liners and exposed to ultra-violet radiation from an Oriel 50 watt mercury arc lamp (Oriel Corp., Stratford, Conn.) or a Sylvania Blacklight fluorescent bulb (Sylvania 350 BL bulb, Siemens Corp./Osram Sylvania Inc., Danvers, Conn.) for 30–60 minutes at approximately 23° C. The polymeric films were further heated at 60–70° C. for approximately 30 minutes, then baked at 120° C. in an oven for several hours to ensure complete cure. The release liners were removed and the films were dried in a forced-air oven at 105° C. for at least 4 hours but not longer than 10 hours. The glass transition temperature (Tg) of each sample was determined by Differential Scanning Calorimetry using a Perkin-Elmer 7-Series Thermal Analysis System (Perkin-Elmer Corp., Norwalk, Conn.) with a general temperature range of −50 to 200° C. Tg values were determined according to ASTM protocol E 1356-91 except a 20° C./minute ramp was used. If a transition could not be found in the general range, the temperature range was expanded as needed. Measurements were made after two heat and cool cycles. The Tg was recorded as a midpoint determination of the point at which the derivative of the interpolated slope of the transition equaled zero.

Refractive Index (n$_\lambda$)

The index of refraction was determined by inserting an optical fiber capable of carrying light at the required wavelength n$_\lambda$ (typically, an 8 mW continuous wave laser diode at 1300 nm) into a liquid monomer or mixture of monomers, polymerizing the monomer(s) as described above to obtain a polymer, and measuring the intensity of the back reflection from the interface of the fiber and the sample. This was compared to the intensity of back-reflection when the same fiber was immersed in a material of known index (water) at the probing wavelength. Using the value of the refractive index of the fiber itself, the index of the probed material was calculated. Solid materials were first melted and the fiber inserted. In order to increase sensitivity of the measurements, the intensity of the incident light was modulated with a square-wave generator from a function generator (HP 8013A Pulse Generator, Hewlett Packard Instruments, Palo Alto, Calif.) and the detected signal analyzed using a lock-in detector (Stanford Research Systems Model SR510 Lock-In Amplifier, Stanford Research Systems Inc., Sunnyvale, Calif.) which was given the same square-wave reference signal. The refractive index measurements were reproducible to ±0.0015.

Optical Absorbance

Absorbance measurements were made on polymerized cylindrical plugs of sample. The plug typically had a diameter of 0.5 cm and height of 1 cm. Liquefied monomer was doped with 0.2% by weight DEAP, filtered, deoxygenated, and placed in a plastic mold prior to polymerization. Polymerization was effected by exposure to a UV lamp, typically Oriel Model 6281, for 30 minutes followed by heat annealing at 60–80° C. under UV light for an additional time of from 30 minutes to several hours in order to complete the polymerization reaction. Absorbance of the plugs was measured using a UV spectrometer (Model UV-3101PC, Shimadzu Scientific Instruments, Inc., Columbia, Md.) equipped with an integrating sphere. To correct for the loss of probe light intensity due to reflection and scattering from the surface of the plug, which would be measured as an absorption loss, a baseline absorption (the loss recorded at 1050–1070 nm) was subtracted from the entire spectrum.

Example 1

Heptafluoronaphthyl acrylate (Compound V)

For about 3.5 hours, a mixture of 25 g octafluoronaphthalene (PCR Inc.; Gainesville, Fla.), 12 g KOH, and 100 mL tertiary butyl alcohol was refluxed. Water was added, and the tertiary butyl alcohol was distilled from the reaction mixture. The residue remaining in the flask was acidified with HCl and the aqueous mixture was extracted three times with 75 mL dichloromethane. The combined extracts were washed twice with 150 mL distilled water, dried over $MgSO_4$, and rotary evaporated to yield a semi-crystalline solid. Recrystallization from hot hexanes gave 18 g heptafluoro-2-naphthol (72% yield) as slightly tan colored crystals.

In 150 mL acetonitrile, 15 g heptafluoro-2-naphthol was dissolved and cooled to 0° C. before 12 mL triethylamine and 7 mL acryloyl chloride, sequentially, were added slowly by syringe. This resulted in the formation of a light colored precipitate. The reaction was stirred for about two hours at 0° C. and about two hours at room temperature, then poured onto ice and allowed to warm to room temperature and extracted three times with 40 mL dichloromethane. The combined extracts were washed twice with 100 mL distilled water, dried over $MgSO_4$, and rotary evaporated to yield a reddish orange colored oil. Vacuum distillation (75–78° C., 67 Pa) gave 16.3 g (90% yield) of 2-acryloyloxyheptafluoronaphthalene (compound V) as a colorless liquid. A homopolymer prepared as described in Example 13, below, from the acrylate had a refractive index $n_{1.31}$ of 1.523, and average abs/cm of 0.006 (1260–1360 nm) and average abs/cm of 0.12 (1480–1580 nm).

Example 2

1-Pentafluorophenyl-1-pentachlorophenyl-1-acryloyloxyheptafluoroethylether (Compound IV)

Hexachlorobenzene (35 g) was slurried in 160 ml of anhydrous ethyl ether at −40° C. A 2.5 M hexanes solution of n-butyllithium (54.1 mL) was added, and the reaction was stirred for 30 minutes at −40° C. Perfluoro-2-ethoxyacetylfluoride (40 g, 72% pure, prepared from 2-ethoxyethyl acetate by the method described in Example 1 of U.S. Pat. No. 5,326,919, incorporated herein by reference) was added to the −40° C. reaction mixture which was then allowed to warm slowly to room temperature. The reaction mixture was quenched with 200 mL of cold 5% aqueous HCl. The aqueous mixture was extracted with ethyl ether and the extracts were dried over $MgSO_4$ and rotary evaporated to give pentachlorophenyl perfluoroethoxymethyl ketone (49% crude yield). Vacuum distillation (105–109° C., 240 Pa) using a 15 cm Vigreux column gave 19.7 g of a colorless liquid which slowly crystallized on standing.

About 2.1 g magnesium metal turnings (J.T. Baker Inc.; Phillipsburg, N.J.) were dried by heating under a nitrogen purge, cooled, and suspended in 50 mL of anhydrous ethyl ether in a nitrogen atmosphere. A mixture of 8.4 g of chloropentafluorobenzene and 8.1 g of dibromoethane was added dropwise to the suspension. The reaction mixture was stirred at a temperature below 30° C. for 95 minutes in an ice bath. Pentachlorophenyl perfluoroethoxymethyl ketone (19.4 g) dissolved in 20 mL of ethyl ether was added and approximately one half of the ethyl ether was distilled from the reaction flask. Anhydrous 2-methoxyethyl ether (50 mL) was added, and the reaction mixture was heated to 75° C. for one hour. The reaction was quenched with 150 mL of 10% aqueous HCl, extracted with dichloromethane, and the extracts were dried over $MgSO_4$ and rotary evaporated to an oil. Chromatography on a 5×35 cm silica gel column (230–400 mesh, 60 Å) using 4:1 hexane:toluene as the elution solvent gave 15.1 g (61% yield) of 99.9% pure 1-pentafluorophenyl(1-pentachlorophenyl)(2-pentafluoroethoxy)difluoroethanol as a colorless hard wax.

A 14.8 g sample of 1-pentafluorophenyl(1-pentachlorophenyl)(2-pentafluoroethoxy)difluoroethanol in 150 mL of dichloromethane was cooled to 5° C. under a dry nitrogen atmosphere. Acryloyl chloride (2.1 mL) was added, followed by dropwise addition of dry, distilled triethylamine (3.6 mL, J.T. Baker). The reaction mixture was refluxed for 90 minutes, cooled to room temperature, stirred for 14 hours, and quenched with 250 mL of water. The organic layer was collected and rotary evaporated to give a yellow oil. Chromatography on a 5×40 cm silica gel column (230–400 mesh, 60 Å) using 8:1 hexane-ethyl acetate as the eluting solvent gave 12.9 g (80% yield) of 1-pentafluoropheny-1-pentachloropheny-1-acryloyloxyheptafluoro-ethylether (compound IV) as a colorless liquid.

Example 3

1-Acryloyoxy-1, 1-bis(pentafluorophenyl)-2-(2-pentafluoroethoxytetrafluoroethoxy)difluoroethane (Compound X)

About 9.7 g magnesium metal turnings were dried by heating under a nitrogen purge, cooled, and suspended in 250 mL anhydrous ethyl ether in a dry nitrogen atmosphere. A mixture of 40.5 g chloropentafluorobenzene and 37.6 g dibromoethane was added dropwise to the suspension and the reaction mixture was stirred for one hour at less than 30° C. in an ice bath. About 34.8 g perfluoro-2-(2-ethoxyethoxy)acetylfluoride, prepared by direct fluorination of di(ethylene glycol) ethyl ether acetate as described in the previously incorporated Example 1 of U.S. Pat. No. 5,326,919, was added dropwise, and the reaction was stirred at room temperature for 18 hours. The reaction was quenched with dilute aqueous HCl and extracted with dichloromethane. After drying over $MgSO_4$, the solvent was removed by rotary evaporation and the residue was vacuum distilled (136–138° C., 1330 Pa) to give 44.2 g (36% yield) of 1,1-bis(pentafluorophenyl)-2-(2-pentafluoroethoxytetrafluoroethoxy)difluoroethanol as a pale yellow liquid.

A 15.4 g sample of 1,1-bis(pentafluorophenyl)-2-(2-pentafluoroethoxy-tetrafluoroethoxy)difluoroethanol in 50 mL dichloromethane was cooled to 5° C. under an atmosphere of dry nitrogen. Acryloyl chloride (2.05 mL) was added followed by the dropwise addition of 3.5 mL dry, distilled triethylamine. The reaction mixture was refluxed for one hour and an additional 0.35 mL acryloyl chloride and 0.35 mL triethylamine were added. After an additional hour of reflux, the reaction was quenched with water and the organic layer was collected and rotary evaporated to give a pale yellow oil. Chromatography on a 5×40 cm silica gel column (230–400 mesh, 60 Å) using 12:1 hexane-ethyl acetate as the eluting solvent gave 14.4 g 1-acryloyoxy-1, 1-bis(pentafluorophenyl)-2-(2-pentafluoroethoxytetrafluoroethoxy)difluoroethane (88% yield) (compound X) as a colorless liquid.

Example 4

5-Pentafluorophenoxy-3,4,6-trifluoro-2-trifluoromethylphenyl acrylate (Compound VII)

A mixture of 98.4 g pentafluorophenol, 0.1 g sodium saccharin, and 120 mL hexamethyldisilazane was stirred at 73° C. for 17 hours after the initial vigorous reaction. Distillation at 160–61° C. using a 15 cm Vigreux column yielded 119.3 g, 87% of pentafluorophenoxytrimethylsilane, $C_6F_5OSi(CH_3)_3$.

A 56.2 g sample of pentafluorophenoxytrimethylsilane was mixed with 50.0 g octafluorotoluene, 3.0 g anhydrous CsF (Acros Organics: Pittsburgh, Pa.) and 100 mL anhydrous acetonitrile under nitrogen and stirred at reflux. The reaction was followed by GLC for 4 days, with addition of 3.4 g additional hexamethyldisilazane to reconvert traces of pentafluorophenol to the silyl derivative. The mixture was quenched in water, extracted with diethyl ether, dried over $MgSO_4$, and concentrated on a rotary evaporator. The oily residue was distilled (80–100° C., 107 Pa) to give 74.7 g (88% yield) of 4-trifluoromethylnonafluorodiphenyl ether, $C_6F_5OC_6F_4$-4-$CF_3$, and minor amounts of positional isomers thereof.

All of the product from the previous paragraph was mixed with 14.7 g 85% KOH in 250 mL t-butanol, and the mixture was refluxed for 17 hours. The reaction mixture was quenched with dilute aqueous HCl, extracted with $CH_2Cl_2$, dried over $MgSO_4$, and the extracts concentrated on a rotary evaporator. The product was vacuum distilled (97–120° C., 40 Pa) to give 47.8 g (64%) of a mixture of isomers of 2-hydroxy-4-pentafluorophenoxyhexafluorotoluene.

The isomeric mixture (47.8 g) was mixed with 12.5 mL acryloyl chloride in 200 mL cold methylene chloride and treated with 20 mL triethylamine dropwise. The mixture was stirred for 17 hours, filtered, and the filtrate was concentrated on a rotary evaporator. The residue was extracted with ethyl ether and the extracts were filtered and concentrated, and the residue was subjected to flash chromatography on about 450 cm³ of silica gel. Elution with 2000 mL hexanes gave 40.7 g isomeric acryloyloxy-4-pentafluorophenoxyhexafluorotoluenes (75% yield) as a colorless liquid. Based on $^{19}$F-NMR analysis, the main isomer was 2-acryloyloxy-4-pentafluorophenoxyhexafluorotoluene (compound VII).

Example 5

2,4,6-Trichlorodifluorophenyl acrylate (Compound VI)

In a 2 L 3-neck round bottomed flask equipped with an overhead stirrer were placed 120 g (85% pure) KOH, 200 g 1,3,5-trichlortrifluorobenzene (Oakwood Products, Inc.; West Columbia, S.C.), and 600 mL t-butanol. The mixture was stirred and refluxed for 4 hours. Approximately 500 mL 1-butanol was distilled from the reaction mixture. The flask was cooled to room temperature and 600 mL acetonitrile was added. The flask was further cooled in an ice bath and 138 mL acryloyl chloride were added dropwise over the course of two hours. The reaction was stirred for an hour at 0° C. followed by two hours at room temperature. The reaction was then quenched with ice water, acidified with dilute HCl, and extracted with dichloromethane. The extracts were washed with saturated aqueous sodium bicarbonate and distilled water, then dried over $MgSO_4$, filtered, and concentrated on a rotary evaporator. The crude product was vacuum distilled (96–105° C., 13–130 Pa) to give 219 g 2,4,6-trichlorodifluorophenyl acrylate (89.7% yield) (compound VI) as a colorless liquid which crystallized on standing.

Example 6

Bromotetrafluorophenyl acrylate (Compound I)

As in Example 5. 120 g KOH, 110 mL bromopentafluorobenzene (Oakwood Products, Inc.), and 500 mL t-butanol were combined. The mixture was stirred and refluxed for 4 hours and then approximately 400 mL t-butanol was distilled from the reaction mixture. The flask was cooled to room temperature and 500 mL acetonitrile was added. The flask was further cooled in an ice bath and 100 mL acryloyl chloride was added dropwise over the course of an hour. The reaction was stirred for an hour at 0° C. followed by 16 hours at room temperature, then quenched with ice water, acidified with dilute HCl, and extracted with dichloromethane. The extracts were washed with saturated aqueous sodium bicarbonate and distilled water, then dried over $MgSO_4$, filtered, and concentrated on a rotary evaporator. The crude product was vacuum distilled (98–102° C., 1600 Pa) to give 177 g (67% yield) of a mixture of bromopentafluorophenyl acrylate isomers as a colorless liquid. Analysis by $^{19}$F NMR spectroscopy indicated that the major isomer was parcabromopentafluorophenyl acrylate (compound I).

Example 7

1-Acryloyloxy-1-pentafluorophenylperfluorocyclohexane (Compound XI)

Under a nitrogen atmosphere, 60 g bromopentafluorobenzene in 200 mL dry ether were added to 6.32 g magnesium at a rate that maintained a steady reflux. The reaction was stirred for one additional hour. Perfluorocyclohexanone (prepared, for example, as in U.S. Pat. No. 3,321,515, Examples 65–68) (67.5 g) was added in one portion and the reaction allowed to stir for about 16 hours. The reaction mixture was quenched with 200 mL of 10% HCl and extracted twice with 150 mL $CH_2Cl_2$. Drying of the $CH_2Cl_2$ layer (on $MgSO_4$) and rotary evaporation gave an oil. Vacuum distillation (82° C., 80 Pa) gave 74.5 g 1-pentafluorophenylperfluorocyclohexanol (70% yield) as a colorless liquid.

Under a $N_2$ atmosphere, 4.63 mL acryloyl chloride was added via syringe to an ice-cold solution of 21.69 g 1-pentafluorophenylperfluorocyclohexanol in 100 mL dry ether. Triethylamine was distilled from $CaH_2$ and 7.9 mL (56.3 mmol) was added via syringe. The reaction was stirred for 30 minutes in an ice-bath and stirred at room temperature for about 16 hours, then filtered and rotary evaporated to give an oily solid. This was passed through a short path silica gel column with $CH_2Cl_2$ as the eluent to give an oil after evaporation. Vacuum distillation (77–80 ° C., 67 Pa) gave 15.2 g (63% yield) of 1-acryloyloxy-1-pentafluorophenylperfluorocyclohexane (compound XI) as a colorless liquid.

Example 8

1-Acryloyloxy-1-(3,5-dichloro-2,4,6-trifluorophenyl)perfluorocyclohexane (Compound XIII)

Under a $N_2$ atmosphere 29.5 g of 1,3,5-trichloro-2,4,6-trifluorobenzene (Oakwood Products, Inc.) were dissolved in 150 mL dry ethyl ether. The solution was cooled to −78° C. in an acetone/dry-ice bath, then treated with 62.7 mL n-butyllithium (2 M solution in hexanes) over a two-hour period. Stirring was continued for 3 hours at −78° C. Via syringe, 34.8 g perfluorocyclohexanone were added, and the mixture was stirred at room temperature for 16 hours. The reaction was quenched with dilute HCl and extracted with ethyl ether, and the extracts were dried (using $MgSO_4$) and rotary evaporated. Vacuum distillation (118–120° C., 80–110 Pa) gave 37.3 g 1-(3,5-dichloro-2,4,6-trifluorophenyl) perfluorocyclohexanol (62% yield) as a colorless liquid.

Under a N$_2$ atmosphere, 4.43 mL acryloyl chloride were added via syringe to an ice-cold solution of 20 g 1-(3,5-dichloro-2,4,6-trifluorophenyl)perfluorocyclohexanol in 150 mL dry ethyl ether. Via syringe, 7.6 mL triethylamine (freshly distilled from CaH$_2$) was added, stirring was continued for 10 minutes in the ice-bath, after which the reaction mixture was stirred at room temperature for about 18 hours. The reaction mixture was filtered and the residue washed with petroleum ether. The filtrate and washes were combined and rotary evaporated to give an oil that was vacuum distilled (112–119° C., 80 Pa) to give 12 g (54% yield) of 1-acryloyl-1-(3,5-dichloro-2,4,6-trifluorophenyl) perfluoro-cyclohexane (compound XIII) as an oil that solidified on standing.

Example 9

2-Acryloyloxy-1-{(2-trifluoromethoxytetrafluoroethoxy) tetrafluoroethoxy}-2-pentachlorophenylpentafluoropropane (Compound IX)

Under a nitrogen atmosphere, 21.4 g hexachlorobenzene was suspended in 200 mL dry ethyl ether and the reaction flask was cooled to −40° C. in an acetonitrile/dry-ice bath. A 1.6 M hexanes solution (47.1 mL) of ii-butyllithium was added by syringe and the reaction was stirred at −40° C. for two hours. A 35 g sample of 1-{(2-trifluoromethoxytetrafluoroethoxy)tetrafluoroethoxy}pentafluoroacetone, prepared by the method as described in Example 23, below, was added in one portion and the reaction was allowed to come to room temperature while stirring for about 16 hours). The reaction was quenched with dilute aqueous HCl and the mixture was extracted with ethyl ether. The extract was dried (with MgSO$_4$) and rotary evaporated to give an oil. Vacuum distillation (133–135° C., 160 Pa) gave 10 g 1-{(2 -trifluoromethoxytetrafluoroethoxy) tetrafluoroethoxy}-2-pentachlorophenylpentafluoro-2-propanol (18% yield) as a colorless liquid.

Under an N$_2$ atmosphere, an ice-cold solution of 8.12 g of the above perfluoro alcohol in 100 mL dry ethyl ether was treated with 1.03 mL acryloyl chloride via syringe. Triethylamine (1.8 mL, distilled from CaH$_2$) was added via syringe, and the reaction was stirred at room temperature for about 16 hours. The reaction mixture was filtered and rotary evaporated to an oily solid. The oily solid was extracted with petroleum ether and the extracts were concentrated to a viscous oil. This oil was vacuum distilled (140–143° C., 120 Pa) to give 5.5 (63% yield) of 2-acryloyloxy-1-{(2-trifluoromethoxytetrafluoroethoxy)tetrafluoro-ethoxy}-2-pentachlorophenylpentafluoropropane (compound IX) as a colorless oil.

Example 10

Acryloyloxychlorooctafluorodiphenyl ether (isomeric mixture)

A mixture of 4.00 g pentafluorophenol, 4.00 g chloropentafluorobenzene, 0.12 g 18-crown-6 ether, 1.4 g powdered 85% KOH, and 15 mL diglyme was stirred at 130° C. for 18 hours. The cooled mixture was washed with water, extracted with methylene chloride, and the extracts rotary evaporated to yield 4.6 g of a sticky solid. Vacuum distillation (85–95° C., 33 Pa) of the combined residues from several condensations yielded 23.6 g of solid product that melted at 58–63° C. Analysis by GC/MS showed the solid to be a mixture of two chlorononafluorodiphenyl ether isomers.

The chlorononafluorodiphenyl ethers (23.4 g) were mixed with 8.4 g of 85% KOH in 150 mL t-butanol and the mixture was refluxed for 17 hours. The reaction mixture was quenched with dilute HCl, extracted with CH$_2$Cl$_2$, dried over MgSO$_4$, and concentrated on a rotary evaporator. The product was vacuum distilled (35° C., 66 Pa) to give 19.6 g (84%) of a mixture of seven chlorohydroxyoctafluorodiphenyl ether isomers which were confirmed by spectroscopic analysis.

The isomeric chlorohydroxyoctafluorodiphenyl ether mixture was mixed with 6.0 mL acryloyl chloride in 250 mL cold methylene chloride and 10 mL triethylamine was added dropwise. The mixture was stirred for 17 hours, filtered, and the filtrate was rotary evaporated. The residue (27.1 g) was extracted with ethyl ether and the extracts were filtered and concentrated on a rotary evaporator. This residue was subjected to flash chromatography on about 450 cm$^3$ of silica gel and eluted with hexanes to give 14.8 g (65% yield) of a mixture of seven isomers of chloro(acryloyloxy) octafluorodiphenyl ether as a colorless liquid confirmed by spectroscopic analysis.

Example 11

2-Acryloyloxy-2-pentafluorophenyl-3-( 1,2,2-trichloro- 1,2-difluoroethoxy)pentafluoropropane An ethereal solution of pentafluorophenyl magnesium bromide was prepared under a N$_2$ atmosphere by the addition of 1 mL of a solution of 12.9 g bromopentafluorobenzene in 20 mL ethyl ether to 1.3 g magnesium. An exothermic reaction ensued and the remaining bromopentafluorobenzene solution was added at such a rate as to maintain a steady reflux. The solution was stirred for an additional 45 minutes, then treated with 16.7 g 1-(1,2,2-trichloro-1,2-difluoroethoxy)perfluoroacetone (84% pure), prepared as described in Example 21, below, and the mixture was stirred at room temperature for 72 hours. The reaction was quenched with 200 mL of 10% aqueous HCl and extracted with 150 mL dichloromethane. The extract was dried over MgSO$_4$ and concentrated to an oil by rotary evaporation. Vacuum distillation (75–80° C., 67 Pa) of the oil gave 14 g 2-pentafluorophenyl-3-(1,2,2-trichloro-1,2-difluoroethoxy)pentafluoro-2-propanol (55% yield) as a colorless liquid.

A 12.2 g sample of the propanol prepared above was dissolved in 50 mL dry ethyl ether under a nitrogen atmosphere and the solution was cooled in an ice bath. Acryloyl chloride (2.4 mL) was added by syringe. Triethylamine (3.0 g), distilled from CaH$_2$, was then added by syringe and the reaction was stirred for 30 minutes at 0° C. The ice bath was removed and the reaction was stirred for an additional 2 hours. The reaction was filtered and the filtrate was washed twice with 25 mL water, then dried over MgSO$_4$ and rotary evaporated to an oily solid. The solid was dissolved in dichloromethane and filtered through silica gel and the filtrate was rotary evaporated to an oil. The oil was vacuum distilled (100–105° C., 67 Pa) to give 2-acryloyloxy-2-pentafluorophenyl-3-(1,2,2-trichloro-1,2-difluoroethoxy) pentafluoropropane (5.85 g, 43% yield) as a colorless liquid.

Example 12

1,2-bis(acryloyloxy)tetrabromobenzene (Compound XXIII)

Tetrabromocatechol (25 g) was dissolved in 250 mL acetonitrile and the solution was cooled to 0° C. in an ice bath. Triethylamine (17 mL) was added and the mixture was stirred at 0° C. for two hours. Acryloyl chloride (10 mL) was added dropwise by syringe, the ice bath was removed, and the reaction was stirred for 16 hours. The reaction was quenched with ice water and was acidified with dilute aqueous HCl to give a cream colored precipitate. The precipitate was collected by filtration and washed with water. Crystallization from hot methanol gave 20.6 g 1,2-bis(acryloyloxy)tetrabromobenzene (66% yield) as fine, colorless needles. The product had a melting point of 135–37° C.

Example 13

Preparation of polymners

To prepare polymers useful in the invention, liquidified monomers (or monomer mixtures) were doped with 0.2–0.5% by weight, based upon the total weight of polymerizable monomer(s), of a photoinitiator, preferably PhC(O)CH(OCH$_2$CH$_3$)$_2$ (DEAP), syringe-filtered, deoxygenated and exposed to UV radiation from an Oriel™ 50 watt mercury arc lamp or a Sylvania Blacklight fluorescent bulb (Sylvania 350BL bulbs, Siemens Corp./Osram Sylvania Inc., Danvers, Conn.) for 30–60 minutes. The samples were typically heated to temperatures above their glass transition temperature during and after light exposure to ensure an acceptable extent of curing. Heating was effected either with an IR heat lamp or in a convection oven.

Representative homopolymers prepared according to this example are shown in Table 1, above, along with observed absorbance/cm$^{-1}$ for the homopolymers. Table 2 shows refractive index and optical absorbance data for selected copolymers of the invention (the structure of whose monomers has been shown above), prepared as described in this example.

above the hot plate. Portions, approximately 25 mm square, were cut from each film sample and weighed. The square portions were then immersed in pentafluorophenyl acrylate for 15 minutes, rinsed with isopropanol, blown dry for 10 seconds with a stream of nitrogen gas, and weighed. The weight gain upon immersion in pentafluorophenyl acrylate monomer was taken as a measure of the amount of swelling of the polymer film. The results are shown in Table 3A; each entry represents the average of at least two separate measurements.

TABLE 3A

| Crosslinker | Crosslinker amount, wt % | Average wt gain, % |
| --- | --- | --- |
| TMPTA | 5 | 55 |
| HFPDDA | 5 | 44 |
| TFHQDA | 5 | 18 |
| TMPTA | 10 | 2 |
| HFPDDA | 10 | 10 |
| TFHQDA | 10 | 7 |

The data of Table 3 show that fluorinated crosslinkers, especially tetrafluorohydroquinone diacrylate, are useful in reducing the swelling of polymerized fluorinated acrylate compositions when placed in contact with fluorinated acrylate monomers. Reduction in swelling was related to increased dimensional stability of the polymer.

In a similar fashion, two crosslinkers, TMPTA and FPEGDA, were evaluated separately using a mixture of pentafluorophenyl acrylate and (perfluorocyclohexyl) acrylate (86/14 wt %). FPEGDA refers to

TABLE 2

| Monomer 1 | | Monomer 2 | | Co-polymer n(1.31) | Copolymer average abs/cm[1] | | Copolymer abs/cm >0.01[2] | |
| --- | --- | --- | --- | --- | --- | --- | --- | --- |
| Compd # | Wt % | Compd # | Wt % | | 1260–1360 nm | 1480–1580 nm | 1260–1360 nm | 1480–1580 nm |
| I | 44.06 | XI | 55.74 | 1.474 | .0045 | .018 | 1340–1360 | 1480–1580 |
| VII | 83.22 | X | 16.59 | 1.447 | .002 | .005 | 1345–1360 | none |
| Ex. 10 | 45.4 | X | 54.6 | 1.459 | .004 | .005 | 1355–1360 | none |
| Ex. 10 | 48.46 | XI | 51.34 | 1.458 | .0025 | .01 | 1350–1360 | 1480–1500 |
| VI | 31.2 | XI | 68.8 | 1.459 | .006 | .013 | 1345–1360 | 1480–1580 |

[1]average abs/cm was the average light absorption per centimeter over the wavelength region noted. The target value was <0.01.
[2]abs/cm >0.01 indicated those parts of the wavelength region where absorption/cm exceeded 0.01.

The data of Table 2 show that essentially identical refractive indexes can be obtained for a number of copolymers having distinctly different makeup and low optical absorbances in the desired wavelength ranges can be achieved.

Example 14

Crosslinked Copolymers

Monomer solutions of pentafluorophenyl acrylate containing various weight percentages of three different crosslinkers, trimethylolpropane triacrylate (TMPTA), 1,1,5,5-tetrahydrohexafluoropentane-1,5-diol diacrylate (HFPDDA), and tetrafluorohydroquinone diacrylate (TFHQDA), and 0.2 weight percent 2,2-diethoxyacetophenone photoinitiator, were prepared. Polymer films, approximately 0.05 mm thick, were prepared from the mixtures by placing the monomer solutions between polycarbonate release liners that were then warmed to 80° C. on a hot plate and irradiated for 30 minutes with the light from two 15 watt fluorescent black lights (F15T8-BLB, General Electric Co., Schenectady, N.Y.) held 7.6 cm $CH_2=CHCOOCH_2(CF_2OCF_2)_nCH_2OCOCH=CH_2$, n~6–12 made by acrylation of the diol prepared as in U.S. Pat. No. 5,384,374 by direct fluorination of diacetate of poly(ethylene glycol) (av. No. molecular wt of ~600), methanolysis, and reduction with NaBH4. Because of its high molar volume, FPEGDA had very low optical loss in the infrared regions of interest. Polymer films were tested as above for swelling by pentafluorophenyl acrylate and the data are shown in Table 3B.

TABLE 3B

| Crosslinker | Crosslinker amount, wt % | Wt % PFPA Absorbed |
| --- | --- | --- |
| TMPTA | 4 | 45 |
| FPEGDA | 5 | 79 |

Example 15

Preparation of Haloacrylates and Homopolymers Thereof

Halogenated acrylates of the invention include those based upon the reaction of acryloyl chloride with: 1) perhalogenated tertiary carbinols, 2) perhalogenated phenols, and 3) perhalogenated naphthols; and 4) perhalogenated thiophenols.

Properties of homopolymers of halogenated acrylates having general formula XXIX based upon the esterification of acrylic acid with perhalogenated tertiary carbinols are shown in Table 4:

$$CH_2=CHC(O)OCR^{10}R^{11}R^{12} \qquad \text{XXIX}$$

Haloacrylates described in Table 4 were prepared according to methods described in Examples 2, 3, 7, 8, 9, and 11. Their structures were confirmed by spectroscopic analysis.

TABLE 4

| | | | | | Homopolymer | | | |
| | | | | | average abs/cm[1] | | average abs/cm >0.01[2] | |
| Cpd | $R^{10}$ | $R^{11}$ | $R^{12}$ | $n_{1.31}$ | 1260–1360 nm | 1480–1580 nm | 1260–1360 nm | 1480–1580 nm |
| --- | --- | --- | --- | --- | --- | --- | --- | --- |
| 4-1 | $CF_3$ | $CF_3$ | $C_6F_5$ | 1.416 | .004 | .009 | 1350–1360 | 1575–1580 |
| 4-2 | $CF_3$ | $CFCl_2CFClOCF_2$ | $C_6F_5$ | 1.441 | .003 | .003 | 1355–1360 | none |
| 4-3 | $CF_2Cl$ | $ClCF_2CF_2OCF_2$ | $C_6F_5$ | 1.426 | — | — | — | — |
| 4-4 | $CF_2Cl$ | $CF_2Cl$ | $C_6F_5$ | 1.459 | — | — | — | — |
| 4-5 | $C_4F_9OCF_2$ | $C_4F_9OCF_2$ | $C_6F_5$ | 1.368 | — | — | — | — |
| 4-6 | $CF_3$ | $C_6F_{13}$ | $C_6F_5$ | 1.380 | .003 | -.006 | 1357–1360 | none |
| 4-7 | —$CF_2CF_2CF_2CF_2CF_2$— | | $C_6F_5$ | 1.418 | .004 | .002 | 1340–1360 | none |
| 4-8 | —$CF_2CF_2CF(Cl)CF_2CF_2$— | | $C_6F_5$ | 1.430 | — | — | — | — |
| 4-9 | —$CF_2CF_2CF_2CF_2CF_2$— | | $C_6F_3Cl_2$ | 1.446 | .003 | .003 | 1345–1360 | none |
| 410 | —$CF_2CF_2CF_2CF_2CF_2$— | | $C_6F_4Cl$ | 1.423 | — | — | — | — |
| 4-11 | $CF_3$ | $CF_3$ | $C_6Cl_5$ | 1.530 | — | — | — | — |
| 4-12 | —$CF_2CF_2CF_2CF_2CF_2$— | | $C_6Cl_5$ | 1.500 | — | — | — | — |
| 4-13 | $CF_3$ | $CF_3OCF_2$ | $C_6Cl_5$ | 1.506 | — | — | — | — |
| 4-14 | $CF_3$ | $CF_3O$-i-$C_3F_6OCF_2$ | $C_6Cl_5$ | 1.450 | .002 | .004 | 1355–1360 | none |
| 4-15 | $CF_3$ | $CF_3O(C_2F_4O)_2CF_2$ | $C_6Cl_5$ | 1.444 | — | — | — | — |
| 4-16 | $C_2F_5OCF_2$ | $C_2F_5OCF_2$ | $C_6Cl_5$ | 1.449 | — | — | — | — |
| 4-17 | $C_4F_9OCF_2$ | $C_4F_9OCF_2$ | $C_6Cl_5$ | 1.420 | — | — | — | — |
| 4-18 | $C_4SCl_3$ | $CF_2Cl$ | $CF_2Cl$ | 1.525 | — | — | — | — |
| 4-19 | $C_4SCl_3$ | $CF_3$ | $C_6F_{13}$ | 1.435 | — | — | — | — |
| 4-20 | $C_6F_5$ | $C_2F_5$ | $C_6F_5$ | 1.441 | — | — | — | — |
| 4-21 | $C_6F_5$ | $C_2F_5OC_2F_4OCF_2$ | $C_6F_5$ | 1.424 | .006 | .06 | 1350–1360 | 1480–1580 |
| 4-22 | $C_6F_5$ | $CFCl_2CFClOC_2F_4$ | $C_6F_5$ | 1.450 | — | — | — | — |
| 4-23 | $C_6F_5$ | $C_2F_5OC_2F_4OCF_2$ | $C_6Cl_5$ | 1.470 | — | — | — | — |
| 4-24 | $C_6F_5$ | $C_2F_5OCF_2$ | $C_6Cl_5$ | 1.488 | — | — | — | — |
| 4-25 | $C_2F_5OCF_2$ | $C_2F_5OCF_2$ | $C_6F_5$ | 1.390 | — | — | — | — |
| 4-26 | —$CF_2CF_2CF_2CF_2CF_2$— | | $C_6Cl_2F_2$—$(OC_6F_5)$ | 1.462 | — | — | — | — |

[1]average abs/cm was the average light absorption per centimeter over the wavelength region noted. The target value was <0.01.
[2]abs/cm >0.01 indicated those parts of the wavelength region where absorption/cm exceeded 0.01.4

The data of Table 4 and Table 5, below, show that the refractive index of homopolymers of the invention can be tailored dependent upon choice of halogenated groups in the structure.

Properties of halogenated acrylates having general formula XXX, based upon the reaction of acryloyl chloride with perhalogenated phenols are shown in Table 5:

XXX

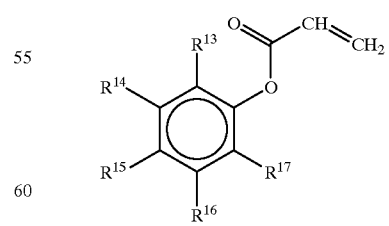

Haloacrylates described in Table 5 were prepared according to methods described in Examples 4, 5, 6, and 10. Their structures were confirmed by spectroscopic analysis.

TABLE 5

| Cmpd | $R^{13}$ | $R^{14}$ | $R^{15}$ | $R^{16}$ | $R^{17}$ | $n_{1.31}$ | Average Abs/cm[1] 1260–1360 nm | Average Abs/cm[1] 1480–1580 nm | Average Abs/cm >0.01[2] 1260–1360 nm | Average Abs/cm >0.01[2] 1480–1580 nm |
|---|---|---|---|---|---|---|---|---|---|---|
| 5-1 | F | F | F | F | F | 1.465 | — | — | — | — |
| 5-2 | F | F | Cl | F | F | 1.500 | — | — | — | — |
| 5-3 | F | F | $CF_3C_6F_4S$ | F | F | 1.499 | — | — | — | — |
| 5-4 | F | F | $ClC_6F_4O$ | F | F | 1.503 | .006 | .007 | 1348–1360 | 1480–1500 |
| 5-5 | F | F | $BrC_6F_4O$ | F | F | 1.512 | — | — | — | — |
| 5-6 | F | F | $(C_6F_5)CO_2$ | F | F | 1.474 | — | — | — | — |
| 5-7 | $CF_3$ | F | F | $C_6F_5O$ | F | 1.465 | .002 | .008 | 1352–1360 | 1480–1500 |
| 5-8 | $CF_3$ | F | F | $ClC_6F_4O$ | F | 1.505 | — | — | — | — |
| 5-9 | F | F | $CF_3$ | F | F | 1.444 | — | — | — | — |
| 5-10 | F | F | $C_6F_5$ | F | F | 1.477 | — | — | — | — |
| 5-11 | Cl | F | Cl | F | Cl | 1.547 | .003 | .005 | 1350–1360 | 1480–1485 |
| 5-12 | Cl | Cl | Cl | Cl | Cl | 1.550 | — | — | — | — |
| 5-13 | F | F | CN | F | F | 1.499 | — | — | — | — |
| 5-14 | F | F | $C_6F_5S$ | F | F | 1.508 | — | — | — | — |
| 5-15 | F | F | I | F | F | 1.548 | — | — | — | — |
| 5-16 | Br | F | Br | F | F | 1.558 | — | — | — | — |
| 5-17 | F | F | Br | F | F | 1.515 | .004 | .012 | 1350–1360 | 1480–1580 |
| 5-18 | Br | F | F | Cl | F | 1.544 | — | — | — | — |
| 5-19 | $CF_3$ | F | F | Br | F | 1.487 | — | — | — | — |

[1] average abs/cm was the average light absorption per centimeter over the wavelength region noted. The target value was <0.01.
[2] abs/cm >0.01 indicated those parts of the wavelength region where absorption/cm exceeded 0.01.4

A perfluorothioacrylate corresponding to formula XXXI was prepared in a manner essentially as described previously by reaction of acryloyl chloride with pentafluorothiophenol (c.f, Examples 1, 5, 6, etc.).

XXXI

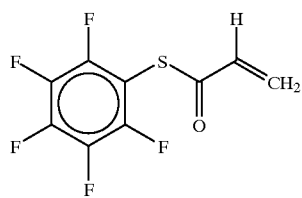

Compound XXXI had a melting point of less than 25° C., and the refractive index ($n_{1.31}$) of the corresponding homopolymer was 1.516.

Example 16

Preparation of 1,3,5-tribromo-2,4-bisacryloyloxybenzene

Ten grams of 2,4,6-tribromoresorcinol was dissolved in 150 mL of acetonitrile and the mixture was cooled to 0° C. Acryloyl chloride (4.7 mL) was added and the mixture was magnetically stirred. Triethyl amine (8.0 mL) was then added in a dropwise fashion and the reaction was maintained at 0° C. A precipitate formed upon addition of triethyl amine. After the triethyl amine addition, the reaction was stirred for one hour at 0° C. and 24 hours at room temperature. The reaction mixture was filtered and the filtrate was rotary evaporated to a brownish oily solid. The solid was washed with water and crystallized from hot hexanes to give 12 g (91%) of 1,3,5-tribromo-2,4-bisacryloyloxybenzene as colorless crystals.

Example 17

Preparation of tribromopyrogallol triacrylate (Compound XXV)

Pyrogallol (10 g) was dissolved in 150 mL of diethyl ether and bromine (12 mL in 50 mL of dichloromethane) was added dropwise over a 2 hour period to the stirred solution. The resulting reddish homogeneous solution was stirred for 16 hours. The reaction mixture was then rotary evaporated to a light red-brown semicrystalline solid. The solid was dissolved in 200 mL of diethyl ether and the solution was filtered. Heptane (200 mL) was added to the filtrate and the slightly cloudy solution was allowed to slowly evaporate to form fine, off-white needles of tribromopyrogallol (27.7 g, 96%).

Ten grams of tribromopyrogallol was dissolved in 200 mL of acetonitrile and the mixture was cooled to 0° C. Acryloyl chloride (8 mL) was added and the mixture was magnetically stirred. Triethyl amine (13 mL) was then added in a dropwise fashion and the reaction was maintained at 0° C. A precipitate formed upon addition of triethyl amine. After the triethyl amine addition, the reaction was stirred for one hour at 0° C. and 16 hours at room temperature. The reaction mixture was filtered and the filtrate was rotary evaporated to a yellowish oil. The oil was washed with water and crystallized from hot hexanes to give 6.2 g (43%) of tribromopyrogallol triacrylate as colorless needles.

Example 18

Preparation of tribromophloroglucinol triacrylate (Compound XXIV)

Phloroglucinol dihydrate (10 g) was suspended in 150 mL of dichloromethane and bromine (12 mL in 50 mL of dichloromethane) was added dropwise over 2.5 hour period to the stirred suspension. The suspended phloroglucinol dissolved during the course of the bromine addition. After stirring for an additional 2 hours a two-phase solution was obtained. The pale orange dichloromethane supernatant solution was decanted from a small amount of a denser, dark red aqueous solution. The dichloromethane solution was rotary evaporated to a pinkish colored semicrystalline solid. The solid was dissolved in a 50 mL of acetone and 500 mL of heptane was slowly added with stirring to give beige crystals of tribromophloroglucinol (18.8 g, 84%).

Ten grams of tribromophloroglucinol was dissolved in 150 mL of acetonitrile and the mixture was cooled to 0° C. Acryloyl chloride (8 mL) was added and the mixture was magnetically stirred. Triethyl amine (13 mL) was then added in a dropwise fashion and the reaction was maintained at 0° C. A precipitate formed upon addition of triethyl amine. After the triethyl amine addition, the reaction was stirred for one hour at 0° C. and 2 hours at room temperature. The reaction mixture was poured into ice water and a cream colored semicrystalline precipitate formed. The precipitate was collected by filtration, washed with water, and air dried. The solid was crystallized from hot heptanes to give 6.1 g (42%) of tribromophloroglucinol triacrylate as off-white needles.

Example 19

Use of Brominated Crosslinkers to Modify the Refractive Index of Hydrocarbon Acrylates Tetrabromocatechol diacrylate (Example 12) (1.0019 g) was dissolved in 3.9905 g phenoxyethyl acrylate (PEA) (CPS Chemical Co., Old Bridge, N.J.) to give a solution containing approximately 20% by weight of the diacrylate crosslinker. Tribromophloroglucinol triacrylate (Example 18) (0.4995 g) was dissolved in 2.0120 g PEA to give a solution containing approximately 20% by weight of the triacrylate crosslinker. DEAP photoinitiator (0.2% by weight) was added to the solutions and to a sample of pure PEA. Portions of these three samples were polymerized and the refractive indices of the polymers were measured as described above. The polymerized PEA gave a refractive index at 1.31 nm of 1.545. The polymerized PEA/20 wt % tetrabromocatechol diacrylate gave a refractive index at 1.31 nm of 1.561. The polymerized PEA/20 wt % tribromophloroglucinol triacrylate gave a refractive index at 1.31 nm of 1.555. Using the measured refractive index of PEA and calculated densities for the brominated crosslinkers (by methods known in the art), refractive indices were calculated for the homopolymers derived from the brominated crosslinkers. By this method a refractive index at 1.31 nm of 1.693 was calculated for polymerized tetrabromocatechol diacrylate and a refractive index at 1.31 nm of 1.628 was calculated for polymerized tribromophloroglucinol triacrylate. This example shows that the brominated crosslinkers can be used to crosslink acrylate monomers and that they are effective in increasing the refractive index of the resulting polymer.

Example 20

Use of Brominated Crosslinkers to Modify the Glass Transition Temperatures (Tg) of Hydrocarbon Acrylates Tetrabromocatechol diacrylate (Example 12) (0.5084 g) was dissolved in 4.5006 g isobornyl acrylate (IBA) (San Esters Corp., N.Y.) to give a solution containing approximately 10% by weight of the diacrylate crosslinker. Tribromophloroglucinol triacrylate (Example 18) (0.5051 g) was dissolved in 4.4952 g IBA to give a solution containing approximately 10% by weight of the triacrylate crosslinker. DEAP photoinitiator (0.2% by weight) was added to the solutions and to a sample of pure IBA. Portions of these three samples were polymerized and the Tgs of the polymers were measured as described above. The Tg of polymerized IBA was found to be 62.5° C. The Tg of IBA copolymerized with 10 wt % tetrabromocatechol diacrylate was found to be 98.5° C. The Tg of IBA copolymerized with 10 wt % tribromophloroglucinol triacrylate was found to be 96° C. This example shows that the brominated crosslinkers can be used to crosslink acrylate monomers and that they are effective in increasing the glass transition temperature of the resulting polymer.

Example 21

1-(1,2,2-trichloro-1,2-difluoroethoxy) perfluoroacetone

A mixture of 339 g trichloroethanol, 291 g propylene oxide and 17.7 g dry triethylamine was stirred in a 1-liter round bottom flask at 23° C. for four days, then washed with 2×400 mL 10% aq. HCl and 1×400 mL sat. aq. NaCl solution. The remaining organic solution was diluted with 200 mL methylene chloride and dried over $MgSO_4$. The filtered solution was treated with a slight excess of trifluoroacetic anhydride, after which the solvent was removed and the residue distilled at 66° C. and 20 Pa to yield the corresponding trifluoromethyl acetate. The acetate was taken up in perfluoro N-methyl morpholine (PNMM, 3M Company, St. Paul, Minn.) and subjected to direct fluorination, as described in the previously-incorporated Example 1 of U.S. Pat. No. 5,236,919. The fluorinated ester was converted to the corresponding methyl hemi-ketal by addition of $BF_3$/MeOH, and the hemi-ketal was converted to the desired ketone by distillation from conc. $H_2SO_4$. The structure of the ketone was verified by IR and $^{19}F$ NMR spectra.

Example 22

2-Acryloyloxy-2-pentafluorophenylperfluorooctane (Compound VIII)

An ethereal solution of pentafluorophenyl magnesium chloride was prepared from 20.2 g $C_6F_5Cl$, 4.8 g Mg and 100 mL diethyl ether (exothermic after initiation with $BrC_2H_4Br$). A dry-ice condenser was attached and 41.6 g perfluorooctanone (prepared according to the method described in U.S. Pat. No. 5,236,919, Example 1, incorporated herein by reference) was introduced directly into the solution. The reaction mixture was stirred overnight, then treated with dilute aq. HCl and distilled to give 45 g of the desired 2-pentafluorophenylperfluorooctan-2-ol at 78° C./67 Pa. A mixture of 29 g of the alcohol and 4.5 mL acryloyl chloride in 300 mL diethyl ether was treated with 5.05 g triethylamine at 0° C. and allowed to warm to 23° C. overnight with stirring. The reaction mixture was washed with water, dried over $MgSO_4$, and stripped of solvent. Purification on a silica gel column ($CH_2Cl_2/C_6H_{14}$; 1/3) and distillation at 85° C./1.0 Pa gave 21 g colorless liquid acrylate, confirmed by spectroscopic analysis.

Example 23

1-{(2-trifluoromethoxytetrafluoroethoxy) tetrafluoroethoxy}pentafluoroacetone

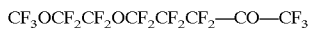

$CF_3OCF_2CF_2OCF_2CF_2CF_2\text{—}CO\text{—}CF_3$

A mixture of 300 g 2-(2-methoxyethoxy)ethanol (Methyl Carbitol™), 174 g of propylene oxide, 17 ml of freshly distilled triethylamine, and 1 g of Adogen™ 464 phase transfer catalyst was sealed in a glass reactor and the mixture was left to stir for 4 days, then heated to 55° C. for 10 hours. Gas chromatography (GC) showed 77% conversion to the desired product with 7.5% starting alcohol and 15% higher homolog. The reaction mixture was diluted with 500 mL of $CH_2Cl_2$ after which 250 mL of acetyl chloride was added dropwise to the stirred mixture with icebath cooling. The organic phase was washed with 700 mL of $H_2O$ and 750 mL saturated NaCl solution. After rotary evaporation, the residue was distilled under vacuum (115 to 135° C./120 Pa) to yield a 247 g of distillate that was 85% pure desired polyether acetate. Direct fluorination of the acetate gave a crude product that was treated with an excess of methanol to form the methyl hemi-ketal ($CF_3OCF_2CF_2OCF_2CF_2OCF_2\text{—}C(OH)(OCH_3)CF_3$). The hemi-ketal was isolated by distillation (245.1 g), then distilled from 250 ml of concentrated $H_2SO_4$. The fraction from 99 to 106° C. (129.1 g) contained 91.6% desired ketone by GC. The material was characterized by IR and fluorine NMR.

Example 24

2,2,2-trichloro-1-(chloro(difluoro)methyl)-1-((2-chloro-1,1,2,2-tetrafluoroethoxy)(difluoro)methyl acrylate (Compound XVII)

In a manner similar to that described as method B by Zeifman et.al., *Izv. Akad. Nauk, Ser. Khim*, 2, 464–468 (1992), 31.5 g of the fluorochloroketone ClCF$_2$CF$_2$OCF$_2$—CO—CF$_2$Cl, synthesized from chloroethanol and epichlorohydrin in the manner described in Example 23, was added to a pre-dried reaction vessel containing 32.7 g of trichloroacetic acid in 100 mL hexamethylphosphoramide at 23° C. The solution was warmed to 60° C. until no additional CO$_2$ evolution was observed, then stirred 14 hours at 23° C. The mixture was quenched with 200 mL of 10% HCl solution and the organic layer was extracted into 100 mL of ethyl ether. The ether fraction was washed with 3×100 mL of dilute HCl solution, dried over MgSO4 and evaporated with rotary evaporation. The residue (42.6 g) was distilled (58–62° C./173 Pa) to yield 7.7 g of carbinol (18%). This material was combined with that from a second run (6.3 g) and the combined carbinol (13.1 g) was dissolved into 50 mL of CH$_2$Cl$_2$ to which was added 3.8 mL of acryloyl chloride with icebath cooling. 4.8 g of dried triethylamine was added dropwise with stirring and the entire mixture was allowed to warm to 23° C. The mixture was washed with saturated NaCl solution, dried over MgSO$_4$, filtered, solvent stripped and then purified by column chromatography (silica gel, 230–400 mesh, 60 Å) using hexanes:ethyl acetate (8:1 by volume). 13 g of clear colorless acrylate was isolated. The structure was confirmed by proton and fluorine NMR and GC/MS. The clear colorless liquid was polymerized to give a clear solid homopolymer having n$_{1.31}$=1.443.

Example 25

2,2,3,3,4,4,5,5,6,6-decafluoro-1-(trichloromethyl)-1-cyclohexanol (Compound XVIII)

A solution of 30 g of perfluorocyclohexanone and 31.7 g of trichloroacetic acid was stirred in a pre-dried reaction vessel containing 113 mL of hexamethylphosphoramide. This mixture was cooled to –10° C. in a dry ice/acetone bath. Slight gas evolution was noted before and during the ketone addition. The stirred milky white reaction mixture was maintained at about 0° C. for an hour and then allowed to warm to 23° C. and stirring was continued 17 hours. The clear yellow solution was quenched with 150 mL of 10% HCl and then transferred to a separatory funnel with 400 mL of ethyl ether. This organic phase was washed with 4×500 mL of dilute HCl and then 300 mL of saturated NaCl solution. The solvent was removed by evaporation. The residue (33.7 g) contained 40.8% product by GC, confirmed by fluorine NMR. This carbinol can be converted to the corresponding acrylate by methods previously described (cf. Example 24).

Example 26

2,2,2-trichloro-1,1-di(2,3,4,5,6-pentafluorophenyl)-1-ethanol and (Compound XIX)

A mixture of 4.9 g of decafluorobenzophenone and 2.7 g of trichloroacetic acid was added to 15 mL of hexamethylphosphoramide. The stirred reaction mixture was maintained at about 0° C. for about 2 hours and then allowed to warm to room temperature and continue stirring at ambient temperature for the next 15 hours. The reaction mixture was characterized by GC and fluorine NMR to show a conversion of approximately 20% to the desired carbinol. This carbinol can be converted to the corresponding acrylate by methods previously described (cf. Example 24).

Example 27

CF$_3$CH(OC(O)CH=CH$_2$)CF$_2$O(CF$_2$)$_4$OCF$_2$CH(OC(O)CH=CH$_2$)CF$_3$ (Compound XXVII)

A solution of 100 g of butane diol and 18, of freshly distilled triethylamine was transferred into a 600 mL Parr reactor, followed by 135.3 g of propylene oxide. The reaction vessel was sealed and the solution was stirred and heated to 50° C. Within the first 35 minutes an exotherm began and the reaction mixture self heated to 140° C. The reaction slowly cooled to 50° C. and was maintained at this temperature for a total of 36 hours. An additional 40 mL of propylene oxide was added and the reaction was re-heated to 50° C. and left with stirring and heating for 24 hours. The contents of the reaction vessel were transferred into a 1000 mL 3-neck round-bottom flask with 150 mL of CH$_2$Cl$_2$. 200 mL of acetyl chloride was added to the stirred mixture with icebath cooling. After the addition, the icebath was removed and the mixture allowed to stir for I hour at 23° C. The mixture was washed with 400 mL of H$_2$O, 400 mL of saturated NaCl solution, then dried over MgSO$_4$. 147.7 g of the desired acetate was isolated by distillation (Bp=124 to 145° C. /160 Pa). The structure was verified by proton NMR. The hydrocarbon acetate was fluorinated, isolated, and converted to the diketone as previously described in Example 23. The diketone can be converted to a diacrylate as described in U.S. Pat. No. 3,520,863, Example 15, incorporated herein by reference.

(Compound XXVIII)

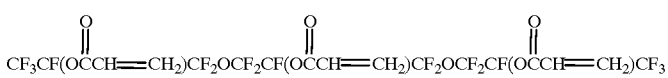

Example 28

150 g of glycerol was weighed into a 600 mL Parr reactor. 250 mL (208 g) of propylene oxide was charged into the glycerol followed by 22.7 mL (16.5 g) of freshly distilled triethylamine. The solution was stirred and heated to 50° C. for one hour, after which the temperature was raised to 70° C. An exotherm followed with a maximum temperature of 135° C. The mixture was stirred at of 70° C. for the next 18 hours. The reactor was cooled to 23° C. and the excess pressure vented into a hood. No glycerol triacetate was observed by GC, so the contents of the reaction vessel were transferred into a 1000 mL 3-neck round-bottom flask with 350 mL of CH$_2$Cl$_2$, and 360 mL of acetyl chloride were added to the stirred mixture with icebath cooling. After the addition, the icebath was removed and the mixture allowed to stir for 1 hour at room temperature. The mixture was washed with 800 mL of H$_2$O, 500 mL of saturated NaCl solution, and dried over MgSO$_4$. rotary evaporation of solvent gave a yellow residue (561.5 g). Distillation (166 to 188° C. /160 Pa) gave 234 g of product that was found to comprise a mixture of 7% trifunctional with 1 propylene oxide group to 1 glycerol group (1:1, PO:Gly), 57% desired tri-functional (2:1, PO:Gly.), 29% trifunctional (3:1, PO:Gly.), and the balance of higher oligomers. The structures were verified by proton NMR. The hydrocarbon acetate was fluorinated, isolated, converted to the corresponding polyketone as previously described in Example 23. The polyketone can be converted to a polyacrylate as described in U.S. Pat. No. 3,520,863, Example 15, incorporated herein by reference.

Example 29

4-Pentafluorobenzoyloxy-2,3,5,6-tetrafluorophenyl acrylate

A mixture of 56.0 g $C_6F_6$ in 300 mL 1 M KOtBu/tBuOH heated at reflux 1 hr, and the organic product was recovered by washing with water and extraction with methylene chloride. The $MgSO_4$-dried extract was stripped on a rotary evaporator to give 48.6 g of tan liquid, 92% $C_6F_5OtBu$ and 4% di-t-butoxytetrafluorobenzene isomers by GC. Of this, 42.4 g was stirred at 60° for 22 hr with 25.0 g powdered KOH in 65 mL t-BuOH. Acidification of an aliquot of the cooled product showed 40% recovery, 20% desired phenol, and 40% byproduct di-t-butoxytetrafluorobenzene isomers. The phenol was separated by washing the reaction product with water and subsequently acidifying the collected water wash to yield 13.0 g of hydroxy-tetrafluorophenyl t-butyl ethers. A prior sample was analyzed by gc/ms and $^{19}F$ NMR and assigned as the para isomer (77%) and meta isomer (23%). 11.6 g was dissolved in 150 mL $CH_2Cl_2$, chilled in ice, treated with 8.0 mL triethylamine, and then treated dropwise with 12.0 g $C_6F_5COCl$. This was left standing for 3 days. Water washing, drying, and stripping gave 21.3 g low-melting solid, pentafluorobenzoyloxytetrafluorophenyl t-butyl ether. This was mixed with 23 mL trifluoroacetic acid and 2 mL water, warmed on a steam bath for 1.5 hr, and quenched in water and extracted with $CH_2Cl_2$, dried, and stripped to 18.6 g tan oil, pentafluorobenzoyloxytetrafluorophenol, confirmed by $^{19}F$ NMR. This was dissolved in 150 mL $CH_2Cl_2$, 5.0 mL acryloyl chloride was added, and the ice-cooled mixture was treated with 10.0 mL triethylamine over about 1 min. Chromatography on 400 mL silica gel with hexane yielded the acylate as a slightly yellow liquid, 11.3 g. The structure of the desired acrylate was confirmed by spectroscopy.

Example 30

3,12-Diacryloxy-3,12-Dihydrido-perfluoro-2,13-Dimethyltetradecane

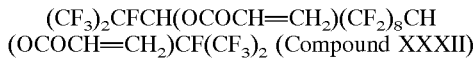
$(CF_3)_2CFCH(OCOCH=CH_2)(CF_2)_8CH(OCOCH=CH_2)CF(CF_3)_2$ (Compound XXXII)

Based on the chemistry reported by Smith, Fawcett, & Coffman, JACS, 84, p4285 (1962); the ketone, $(CF_3)_2CF—CO—(CF_2)_8—CO—CF(CF_3)_2$, was synthesized as follows. 50 g of the di-acid fluoride (F—CO—$(CF_2)_8$—CO—F) was charged into a 600 ml Parr reactor with 0.6 g of anhydrous KF and 54 g of anhydrous diglyme. The reactor was sealed and cooled in dry ice. 33 g of hexafluoropropene was charged into the reactor. The reactor was heated to 100 degrees C over a period of 28 hours. The reactor was cooled and vented and the lower fluorochemical phase isolated (75.6 g, 94% yield) and washed with saturated NaCl solution. The organic was dried over $MgSO_4$, filtered and distilled. A sample of the main cut (colorless clear low melting crystals) was characterized by 19F-NMR and IR. 32 g of this ketone was dissolved in 150 mL of anhydrous diglyme. 3.1 g of $NaBH_4$, suspended in 20 mL of diglyme was added in 1 mL aliquots. The mixture was left to stir for 4 hours with water bath cooling to control the exotherm. The resulting heterogeneous mixture was decomposed with 5% HCl. The lower phase was isolated and the residual diglyme distilled to leave 28.8 g (89% yield) of a yellow solid. This solid was characterized by proton and fluorine NMR and IR to confirm the structure. 24 g of the solid was dissolved in 50 mL anhydrous $CH_2CN$ under a nitrogen atmosphere and charged with 6 g of acryloyl chloride at 5 degrees C. 6.7 g of triethyl amine was added dropwise to the stirred solution. The solid amine hydrochloride by-product was removed by filtration and 100 ml of $CH_2Cl_2$ was added and the organic layer washed with saturated NaCl solution. The organic was then solvent stripped by rotary evaporation to leave the crude diacrylate. The structure was verified by proton and fluorine NMR.

Various modifications and alterations that do not depart from the scope and spirit of this invention will become apparent to those skilled in the art. This invention is not to be unduly limited to the illustrative embodiments set forth herein.

We claim:
1. A halogenated acrylate having the general formula

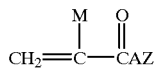

wherein

M is H, $CH_3$, F, Cl, Br, I, or $CF_3$,

A is oxygen or sulfur, and wherein Z is —$CR_fR_f'E$, wherein $R_f$, $R_f^1$, and E are as follows:

$R_f$ and $R_f'$ together are part of a perfluorinated, perchlorinated, or per(chlorofluoro) cycloaliphatic ring group or independently are perfluorinated, perchlorinated, or per(chlorofluoro)
  (a) $C_1$–$C_{20}$ aliphatic groups,
  (b) $C_3$–$C_{20}$ cycloaliphatic groups,
  (c) $C_6$–$C_{20}$ aryl groups,
  (d) $C_7$–$C_{20}$ aralkyl groups, or
  (e) $C_7$–$C_{20}$ alkaryl groups,
  (f) $C_4$–$C_{20}$ heteroaryl groups,
  (g) $C_4$–$C_{20}$ heteroaralkyl groups,
  (h) $C_4$–$C_{20}$ heteroalkaryl groups, wherein heteroatoms can be one or more of O, N, and S atoms, with the proviso that at least one of $R_f$ and $R_f'$ includes one or more of (i) at least one straight-chain $C_4$–$C_{20}$ aliphatic or $C_4$–$C_{20}$ cycloaliphatic group, (ii) at least one ether oxygen atom, and (iii) at least one branched $C_3$–$C_{20}$ aliphatic group, and E is $R_f$,

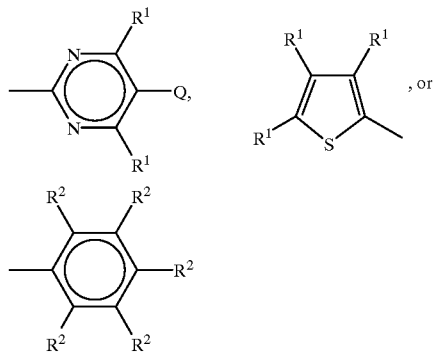

wherein $R^1$, $R^2$, and Q are defined as follows:
each $R^1$ independently is F, Cl, or Br;
each $R^2$ independently is (a) a perfluorinated, perchlorinated, or per(chlorofluoro) group (i), (ii), (iii), (iv), or (v) wherein
   (i) is a $C_1$–$C_{20}$ aliphatic group,
   (ii) is a $C_3$ to $C_{20}$ cycloaliphatic alkyl group,
   (iii) is a $C_6$–$C_{20}$ aryl group,
   (iv) is a $C_7$–$C_{20}$ aralkyl group, and
   (v) is a $C_7$–$C_{20}$ alkaryl group,
(b) F, Cl, Br, I, Q (defined below), $R^4COO$—, —$COOR^4$, —$OSO_2R^4$, or —$SO_2OR^4$, wherein $R^4$ is any group from (a)(i), (a)(ii), (a)(iii), (a)(iv), and (a)(v), or any two adjacent $R^2$ groups together can form a perfluorinated, perchlorinated, or per(chlorofluoro) cycloaliphatic or aromatic ring moiety which optionally can further include n $R^2$ groups where n is a whole number in the range of 0 to 100 that describes the number of free sites on the ring moiety, wherein Q is

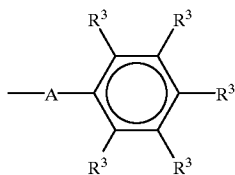

in which A is as defined as above, with the proviso that all $R^2$ groups in the molecule can be the same only when $R^2$ is not Cl, F, Br or I; and each $R^3$ independently can be
(a) a perfluorinated, perchlorinated, or per(chlorofluoro)
   (i) $C_1$–$C_{20}$ aliphatic group,
   (ii) $C_3$–$C_{20}$ cycloaliphatic group,
   (iii) $C_6$–$C_{20}$ aryl group,
   (iv) $C_7$–$C_{20}$ aralkyl group, and
   (v) $C_7$–$C_{20}$ alkaryl group,
(b) F, Cl, Br, I, Q (defined above) $R^4COO$—, —$COOR^4$, —$OSO_2R^4$, or —$SO_2OR^4$, wherein $R^4$ is any group from (a)(i), (a)(ii), (a)(iii), (a)(iv), and (a)(v), or any two adjacent $R^3$ groups together can form a perfluorinated, perchlorinated, or per(chlorofluoro) cycloaliphatic or aromatic ring moiety which optionally can further include n $R^3$ groups where n is a whole number in the range of 0 to 100 that describes the number of free sites on the ring moiety.

2. A halogenated acrylate having the general formula

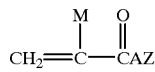

wherein M is H, $CH_3$, F, Cl, Br, I, or $CF_3$, wherein A is O (oxygen) and Z is

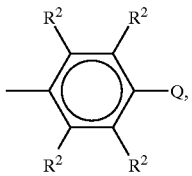

wherein Q is

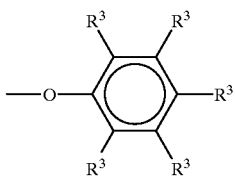

and each $R^2$ and $R^3$ is independently one of F, Cl, and $CF_3$.

3. The halogenated acrylate according to claim 1 wherein A is O.

4. The halogenated acrylate according to claim 3 wherein E is

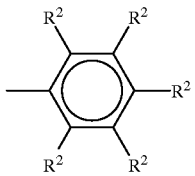

and $R^2$ is previously defined.

5. The halogenated acrylate according to claim 3 wherein each $R_f$ and $R_f'$ is independently a perhalogenated phenyl group and E is a $C_1$–$C_{20}$ perhalogenated aliphatic group comprising at least one ether oxygen atom.

6. The halogenated acrylate of claim 3 wherein $R_f$ and $R_f'$ together form a perhalogenated cyclohexyl group and E is a perhalogenated phenyl group.

7. The halogenated acrylate according to claim 4 wherein each $R^2$ is F.

8. A polymer comprising at least one mer unit derived by polymerization of the olefinic bond from the halogenated acrylate according to claim 1.

9. A polymer comprising at least one mer unit derived by polymerization of the olefinic bond from the halogenated acrylate according to claim 2.

10. An optical device comprising a polymer according to claim 8.

11. An optical device comprising a polymer according to claim 9.

* * * * *

UNITED STATES PATENT AND TRADEMARK OFFICE
CERTIFICATE OF CORRECTION

PATENT NO. : 6,288,266 B1
DATED : September 11, 2001
INVENTOR(S) : Moore, George G.I.

It is certified that error appears in the above-identified patent and that said Letters Patent is hereby corrected as shown below:

<u>Title page,</u>
Item [56], References Cited, OTHER PUBLICATIONS, please add:
-- Adcock, et al., U.S. Govt. Report #AD139958 (1984). (Abstract Only) --

<u>Column 2,</u>
Line 5, "("PEMA")" should read -- ("PMMA") --.

<u>Column 4,</u>
Line 11, "$C_1C_{20}$" should read -- $C_3$-$C_{20}$ --.

<u>Column 5,</u>
Line 5, insert -- a linear -- after "is" and before "perfluoroalkyl".

<u>Column 14,</u>
Line 21, "$C_6F_5MgCl+ R^6_fCOR^6_f \rightarrow \rightarrow R^6_6R^6_fC_6F_5COH$," should read
-- $C_6F_5MgCl+ R^6_fCOR^6_f \rightarrow \rightarrow R^6_fR^6_fC_6F_5COH$, --.

<u>Column 15,</u>
Line 15, "trimesters" should read -- tri-esters --.

<u>Column 16,</u>
Table 1, Example 15, Cpd "XIII." should read Cpd -- XII --.
Table 1, Example 8, insert cdp -- XIII -- before "Example 8".

<u>Column 18,</u>
Line 13, "arornatic" should read -- aromatic --.

<u>Column 22,</u>
Line 20, "pentafluoropheny" should read -- pentafluorophenyl --.
Line 21, "pentachloropheny" should read -- pentachlorophenyl --.

<u>Column 23,</u>
Line 47, "1-butanol" should read -- t-butanol --.

<u>Column 24,</u>
Line 15, "parca-" should read -- para --.

<u>Column 25,</u>
Line 25, "ii-butyllithium" should read -- n-butyllithium --.

UNITED STATES PATENT AND TRADEMARK OFFICE
CERTIFICATE OF CORRECTION

PATENT NO. : 6,288,266 B1
DATED : September 11, 2001
INVENTOR(S) : Moore, George G.I.

It is certified that error appears in the above-identified patent and that said Letters Patent is hereby corrected as shown below:

Column 34,
Line 45, "$CF_3OCF_2CF_2OCF_2CF_2CF_2$-CO-$CF_3$" should read
-- $CF_3OCF_2CF_2OCF_2CF_2OCF_2$-CO-$CF_3$ --.

Column 35,
Line 16, "MgSO4" should read -- $MgSO_4$ --.

Column 36,
Line 44, "Example 28" should be indicated before -- (Compound XXVIII) --.
Line 51, delete -- of --.

Column 38,
Line 3, "$CH_2CN$" should read -- $CH_3CN$ --.

Signed and Sealed this

Tenth Day of June, 2003

JAMES E. ROGAN
*Director of the United States Patent and Trademark Office*